(12) United States Patent
Golombek et al.

(10) Patent No.: US 11,650,169 B2
(45) Date of Patent: *May 16, 2023

(54) SYSTEM AND METHOD FOR MEASURING SOIL PROPERTIES CHARACTERISTICS USING ELECTROMAGNETIC PROPAGATION

(71) Applicant: VAYYAR IMAGING LTD, Yehud (IL)

(72) Inventors: Harel Golombek, Netanya (IL); Shachar Shayovitz, Ness Ziona (IL)

(73) Assignee: VAYYAR IMAGING LTD., Yehud (IL)

( * ) Notice: Subject to any disclaimer, the term of this patent is extended or adjusted under 35 U.S.C. 154(b) by 76 days.

This patent is subject to a terminal disclaimer.

(21) Appl. No.: 17/244,034

(22) Filed: Apr. 29, 2021

(65) Prior Publication Data
US 2021/0262946 A1    Aug. 26, 2021

Related U.S. Application Data

(63) Continuation of application No. 15/749,913, filed as application No. PCT/IL2016/050810 on Jul. 25, 2016, now Pat. No. 11,029,262.

(60) Provisional application No. 62/301,731, filed on Mar. 1, 2016, provisional application No. 62/200,070, filed on Aug. 2, 2015.

(51) Int. Cl.
*G01N 22/04* (2006.01)
*G01N 33/24* (2006.01)

(52) U.S. Cl.
CPC ........... *G01N 22/04* (2013.01); *G01N 33/246* (2013.01); *G01N 2033/245* (2013.01)

(58) Field of Classification Search
CPC . G01N 22/04; G01N 33/246; G01N 2033/245
See application file for complete search history.

(56) References Cited

U.S. PATENT DOCUMENTS

| | | | |
|---|---|---|---|
| 5,908,045 A | 6/1999 | Wallace et al. | |
| 6,289,714 B1 | 9/2001 | Tartre | |
| 9,037,414 B1 | 5/2015 | Pratt | |
| 9,046,461 B1 | 6/2015 | Sohrabi et al. | |
| 2003/0006071 A1 | 1/2003 | Stump et al. | |
| 2007/0273394 A1 | 11/2007 | Tanner et al. | |
| 2015/0053480 A1* | 2/2015 | Kare | G01V 1/166 175/50 |
| 2015/0100168 A1 | 4/2015 | Oliver | |
| 2015/0181315 A1* | 6/2015 | Vuran | H01Q 1/38 340/870.3 |

* cited by examiner

*Primary Examiner* — Marc Anthony Armand
(74) *Attorney, Agent, or Firm* — Browdy & Neimark, PLLC

(57) ABSTRACT

A system and methods for measuring soil properties characteristics, the system comprising: at least one probe configured to be inserted into the soil, the probe comprising a plurality of antennas; a radio link characterization unit for transmitting a radio signal from at least one of the antennas and receiving a propagated radio signal from at least one of the antennas to yield at least one radio link; and a processor for converting the radio link characteristics into the soil properties characteristics.

20 Claims, 21 Drawing Sheets

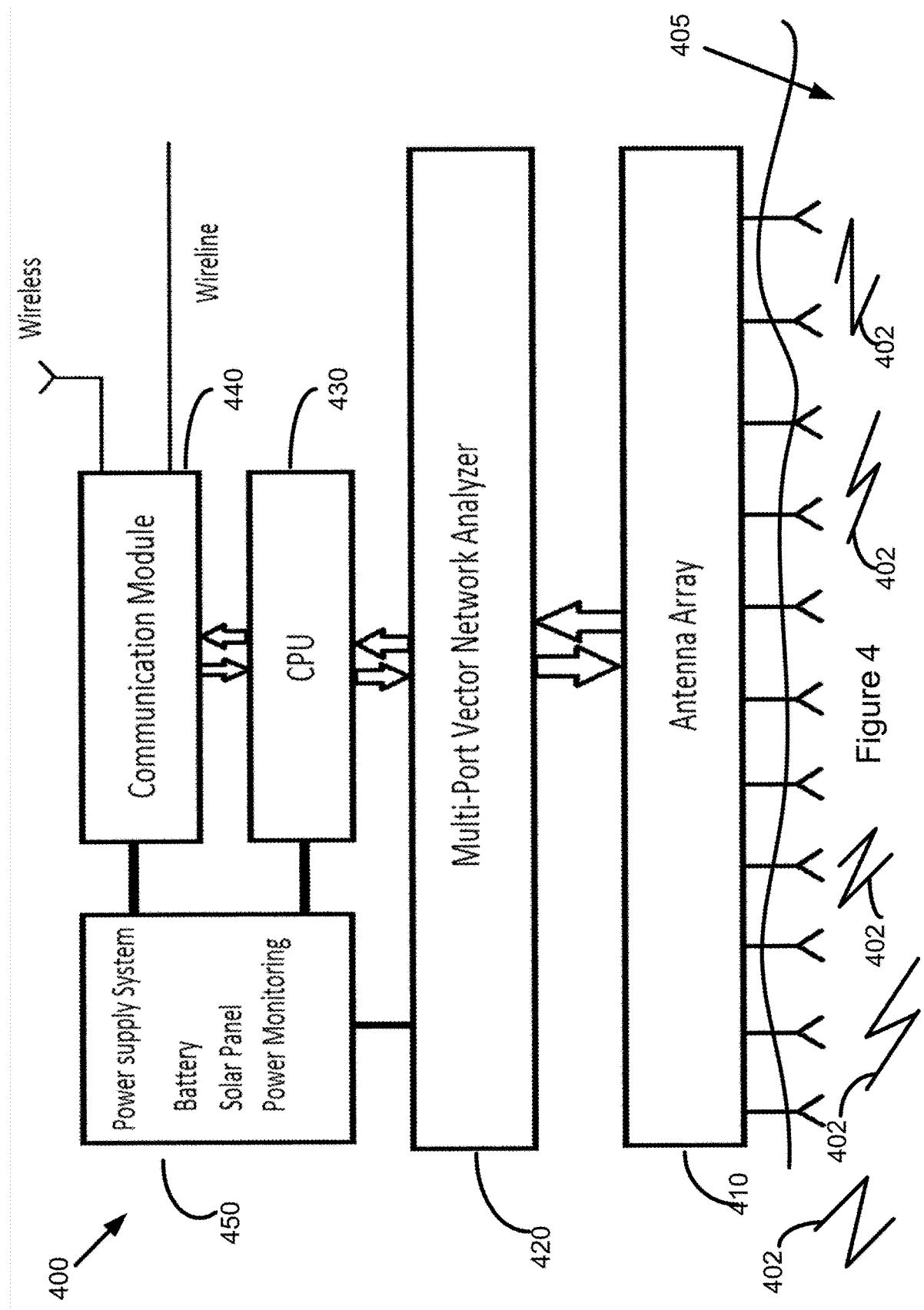

SYSTEM AND METHOD FOR MEASURING SOIL PROPERTIES CHARACTERISTICS USING ELECTROMAGNETIC PROPAGATION

CROSS-REFERENCE

The present application claims the benefit of U.S. Provisional Application Ser. No. 62/301,731, filed on Mar. 1, 2016, entitled "SYSTEM AND METHOD FOR MEASURING SOIL PROPERTIES CHARACTERISTICS USING ELECTROMAGNETIC PROPAGATION", and U.S. Provisional Application Ser. No. 62/200,070, filed on Aug. 2, 2015, entitled "SYSTEM AND METHOD FOR MEASURING SOIL PROPERTIES CHARACTERISTICS USING ELECTROMAGNETIC PROPAGATION" the entire disclosures of which are incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIELD OF THE INVENTION

The present invention relates to a system, device and method for measuring soil content, and more specifically, but not exclusively, to a system, device and method for measuring soil moisture and/or salinity using electromagnetic propagation.

BACKGROUND OF THE INVENTION

Measuring soil moisture and soil salinity is important in many fields, particularly in agriculture to provide farmers with relevant information to manage efficiently their irrigation systems, e.g. use less water to grow a crop, and increase yields and crop quality.

Current methods and systems include using soil moisture sensors to control landscape irrigation. Other fields using soil moisture sensors, include for example Golf courses where sensors are used to increase the efficiencies of their irrigation systems to prevent over watering and leaching of fertilizers and other chemicals offsite.

Examples of prior sensors such as soil moisture sensor technology includes the following systems and devices:

Tensiometers measure the soil moisture tension or suction. This device is a plastic tube with a porous ceramic tip attached at one end and a vacuum gauge on the other end. The porous ceramic tip is installed into the soil at the depth where the majority of the active root system is located. The vacuum gauge measures the soil moisture tension or suction. It measures how much effort the roots must put forth to extract water from the soil and is measured in centibars. The higher the reading, the less moisture that is available and the harder roots must work to extract water. A lower reading indicates more available water. A tensiometer can be used to take manual readings or a special model can be installed to provide the capability for the tensiometer to be wired into the sprinkler system to provide control. Also the tensiometer needs routine maintenance to make sure enough liquid is in the tensiometer and that it hasn't broken tension because the soil has separated away from the ceramic tip. In climates where the ground freezes, tensiometers must be removed and stored for the winter months and reinstalled the following year.

Electrical resistance blocks measure soil moisture tension with two electrodes imbedded in a porous material such as gypsum, or a sand-ceramic mixture. The block allows moisture to move in and out of it as the soil dries or becomes moist. The electrodes measure the resistance to electric current when electrical energy is applied. The more moisture in the block, the lower the resistance reading indicating more available moisture. The blocks use gypsum or similar material to be a buffer against salts (such as fertilizer) that would also affect resistance readings. The sensors using a granular matrix seem to work well and last for a longer time as compared to gypsum blocks.

Electrical conductivity probes measure soil moisture in the soil by how well a current of electricity is passed between two probes. In many ways the concept is similar to resistance blocks but the probes (electrodes) have direct contact with the soil and are not buffered as in resistance blocks. The more moisture in the soil the better the conductivity or the lower the electrical resistance. This method is very sensitive to the spacing of the probes as well as being influenced by soil type and salts that come primarily in the form of fertilizers.

Heat dissipation sensors measure soil moisture by measuring how much heat is dissipated in a ceramic medium. The heat dissipated is directly proportional to the amount of water contained within the ceramic's void spaces. The more water that is contained in the ceramic, the more heat is dissipated and the lower the sensor readings. This corresponds to a higher soil matric potential or in other words, more available water for the plant. The sensor works when water moves in or out of the ceramic due to capillary forces in the soil. The manufacturers claim this type of sensor is independent of soil type or salinity influences.

Dielectric sensors calculate the soil moisture content by measuring the dielectric constant of the soil. A dielectric is a material that does not readily conduct electricity. Dielectric sensors use two different methods to measure soil moisture without measuring electrical conductivity.

Capacitance sensors use frequency-domain-reflectometry and TDR sensors use time-domain-reflectometry. Dielectric sensors are generally expensive and are used more in scientific research than to actually control a lawn sprinkler system.

Capacitance sensors contain two electrodes separated by a dielectric. The electrodes are inserted into the soil or in an access tube in the soil and the soil becomes part of the dielectric. A very high oscillating frequency is applied to the electrodes, which results in a resonant frequency, the value of which depends upon the dielectric constant of the soil. The moisture content of the soil will change the dielectric constant of the soil, therefore more moisture in the soil will change the frequency. This change is converted into a soil moisture measurement.

TDR measures the time required for an electromagnetic pulse to travel a finite distance along a wave guide (steel rods or length of wire) and is dependent upon the dielectric properties of the material surrounding (the soil) the wave guide. As moisture increases in the soil, the time taken for the pulses to travel slows down. The signal is then converted into a soil moisture measurement. This technology is very complex and quite expensive, but seems to provide high accuracy.

The Neutron Probe works by sending out neutrons from a probe (the radioactive source) that is lowered down a tube in preset increments. Neutrons emitted by the probe enter the soil and are thermalized by the hydrogen present in water. These thermalized neutrons enter the helium-3 detector and are registered as a count. As the instrument takes readings of how the neutrons are moving, a calibration is made that converts the neutron count into soil moisture content. The neutron probe needs to be calibrated for each type of soil but it has proven to be very reliable and accurate and is usually the benchmark by which other instruments are compared. However, it is not useful for controlling an irrigation system. This type of sensor, while extremely accurate is not meant to directly control an irrigation system, but rather provide the manager with information upon which water management decisions can be made.

The prior sensors for measuring soil moisture and soil salinity can be less than ideal in at least some respects. Prior sensors such as capacitance sensors must be positioned in a way which provides direct contact (e.g. galvanic contact) between the sensors and the soil to measure for example the impedance of the soil. Also, the prior sensors can be somewhat bulky, difficult to transport and the electrical components can require more alignment than would be ideal in at least some instances.

Additionally, prior sensors have slow response to changes in soil water content or irrigation. The prior sensors have less than ideal resolution, sensitivity and less accuracy than would be ideal, specifically the prior sensors lack of accuracy in sandy soils.

In light of the above, an improved sensor for characterizing and/or measuring soil such as the soil moisture and soil salinity that overcomes at least some of the above mentioned deficiencies of the prior spectrometers would be beneficial. Ideally such a sensor would be compact, integrated with a device or system such as a pierced irrigation pipe, sufficiently rugged and low in cost to be practical for end-user measurements of items, convenient to use.

SUMMARY OF THE INVENTION

Prior to the summary of the invention being set forth, it may be helpful to set forth definitions of certain terms that will be used hereinafter.

The term 'electromagnetic propagation' as used herein is defined as the way the electromagnetic waves travel from a transmitting antenna to a receiving antenna.

According to a first aspect of the invention there is provided a system for measuring soil properties, the system comprising: at least one device configured to be inserted into said soil, said device comprising at least one antenna array, said at least one antenna array comprising a plurality of antennas; a radio link characterization unit for transmitting a radio signal from at least one of said antennas and receiving a propagated radio signal from at least one of said antennas to yield at least one radio link, said radio link comprises a radio frequency propagation in said soil; and at least one processing unit for converting said radio link characteristics into said soil properties characteristics.

In an embodiment, the at least one processing unit is configured with instructions to extract the amplitude and phase of said radio links and compute the soil's dielectric constant and soil conductivity to yield the soil moisture or salinity in at least one layer of said soil.

In an embodiment, the device comprises at least one probe and wherein the at least one antenna array is embedded on said probe.

In an embodiment, the transmitting antenna and receiving antenna are on the same probe.

In an embodiment, the device comprises at least two probes and the transmitting antenna and receiving antenna are on different probes.

In an embodiment, the transmitting antenna and receiving antenna are the same antenna.

In an embodiment, the plurality of antennas are selected from the group consisting of: monopole antennas, dipole antennas, microstrip patch antennas and slot antennas.

In an embodiment, the radio link characterization unit is selected from a group consisting of: a scalar network analyzer, vector network analyzer, an oscilloscope, a time domain reflectometer.

In an embodiment, said soil properties characteristics comprise at least moisture content.

In an embodiment, said soil properties characteristics comprise at least salinity content and moisture content.

In an embodiment, the shape of the probe is selected from the group consisting of:

rod, tube, pipe, pole, screw, double shaped rod.

In an embodiment, the plurality of antennas are placed on the protrusions of the screw thread.

In an embodiment, the probe comprises a first rod and a second rod.

In an embodiment, the first rod and the second rod are parallel to one another.

In an embodiment, half of the antennas of the plurality of antennas are attached to the first rod and half of the antennas are attached to the second rod.

In an embodiment, said plurality of antennas are linearly attached along said first or second rod.

In an embodiment, the device comprises a communication module configured transmit said radio link characteristics or soil properties characteristics to an electronic device.

In an embodiment, said electronic device is selected from a group consisting of:

a tablet, a personal computer, a mobile phone, a smart phone, a smart watch.

In an embodiment, the device is not in direct contact with the soil.

In an embodiment, the device is covered by a protection substance.

In an embodiment, the protection substance is made of plastic.

In an embodiment, the plastic type is selected from the group consisting of: ABS, PVC, Polyethylene, Polypropylene, PTFE (Polytetrafluoroethylene).

According to a second aspect there is provided a method for measuring soil properties characteristics, the method comprising: transmitting one or more radio signals from an antenna array, said antenna array comprising a plurality of antennas attached to at least one probe, said at least one probe is configured to be inserted into said soil;

receiving one or more propagated radio signals from at least one antenna of said antenna array, to yield a plurality of radio links between the plurality of antennas; and converting said plurality of radio links characteristic into soil properties characteristics by at least one processing unit.

In an embodiment, said conversion comprise: extracting the amplitude and phase of said plurality of radio links; calculating the soil's dielectric constant and soil conductivity; calculating the soil moisture or salinity in at least one layer of said soil.

In an embodiment, the method comprising: measuring the soil at a plurality of layers within the soil; and generating a profile of the soil moisture or salinity according the measured time and soil layer.

In an embodiment, the profile comprises graphic profiles shown on a display corresponding to one or more of soil level and corresponding amounts of one or more of soil moisture or salinity.

In an embodiment, the transmitting antenna and receiving antenna are on a single probe.

In an embodiment, the transmitting antenna and receiving antenna are positioned on different probes.

In an embodiment, the transmitting antenna and receiving antenna are the same antenna.

In an embodiment, the plurality of antennas are selected from the group consisting of: monopole antennas, dipole antennas, microstrip patch antennas and slot antennas.

In an embodiment, the radio link characterization unit is selected from a group consisting of: a scalar network analyzer, vector network analyzer, an oscilloscope, a time domain reflectometer.

In an embodiment, said soil properties characteristics comprise at least moisture content.

In an embodiment, said soil properties characteristics comprise at least salinity content.

According to a third aspect there is provided a system for monitoring the growth of a plant in a soil, the system comprising: a device configured to be inserted into said soil, said device comprising a plurality of RF (Radio Frequency) antennas; a radio link characterization unit for transmitting a radio signal from at least one of said antennas and receiving a propagated radio signal from at least one of said antennas to yield at least one radio link; and at least one processing unit for processing said at least one radio link to yield the soil's moisture profile over time; and process said moisture profile to obtain the plant's growth status.

In an embodiment, the at least one processing unit is configured to obtain the plant's root development status.

In an embodiment, the plant is selected from the group consisting of:
corn, wheat avocado, tomato, garlic, onion, any vegetables or fruit According to a forth embodiment there is provided a method for monitoring the development of a plant in a soil, the method comprising: transmitting one or more radio signals from at least one antenna in an antenna array, said antenna array comprising a plurality of antennas attached to a device said device is configured to be inserted into said soil; receiving one or more propagated radio signals from at least one antenna of said antenna array, to yield a plurality of radio links between the antennas in the antenna array; processing said radio links to yield the soil's moisture profile over time; and
processing said moisture profile to obtain the plant's development status.

In an embodiment, said plant's development status comprises said plants roots development or growth status, plant ripeness status.

In an embodiment, said resulted moisture profile over time, is configured to indicate the presence of roots in a given layer in said soil.
In an embodiment, said indication is used by a closed loop irrigation system to control the amount of irrigation supplied to said layer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks, according to embodiments of the invention, could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein, are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The subject matter disclosed may best be understood by reference to the following detailed description when read with the accompanying drawings in which:

FIG. 4 is a high level schematic block diagram illustrating the measuring system, in accordance with examples;

DETAILED DESCRIPTION OF THE INVENTION

Figure 1:
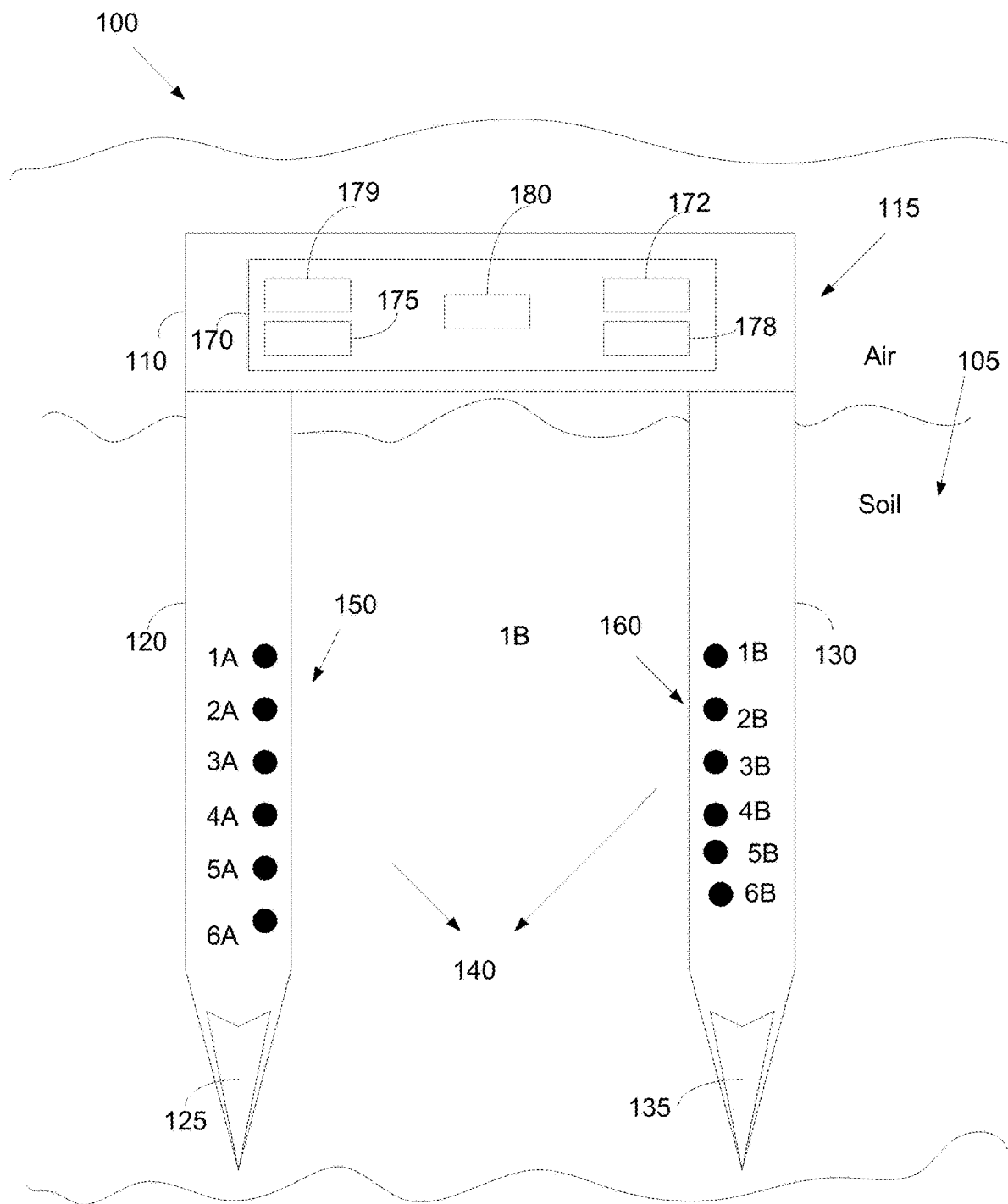
FIG. 1 is a diagram illustrating a system for measuring soil moisture and/or salinity, in accordance with examples.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

A better understanding of the features and advantages of the present disclosure will be obtained by reference to the following detailed description that sets forth illustrative embodiments, in which the principles of embodiments of the present disclosure are utilized, and the accompanying drawings.

As used herein the term arcuate encompasses one or more of curved, elliptical, annular or conical shapes, and portions of these shapes and linear approximations thereof.

As used herein, like characters refer to like elements.

As used herein, "A and/or B" refers to any of A alone, B alone, or a combination of both A and B.

The present invention relates to a system, device and methods for measuring and/or characterizing soil content, and more specifically, but not exclusively, to a system, device and method for measuring soil moisture and/or salinity using electromagnetic propagation.

Generally, electromagnetic radiation is propagating inside any physical material. The speed, magnitude and frequency dispersion of the electromagnetic radiation waves are all significantly dependent on the electrical characteristic of that specific material (e.g. complex dielectric constant). Specifically, the electromagnetic waves propagation in soil is effected by the water and salinity within the soil. Since water content and salinity have a major effect on the electrical complex dielectric constant ($\epsilon=\epsilon'r-j\epsilon''r$), it is possible to extract the water and salinity content, according to the invention, by measuring the wave propagation features as it travels through the soil. More specifically, the propagation speed is determined by the water content in the soil, while the wave attenuation is effected by both water content and soil salinity.

According to one embodiment, there is provided a system, device and methods for measuring soil content such as moisture and/or salinity, the system comprising a holder or housing unit such as a probe comprising a plurality of antennas (e.g. an antenna array or sensor array). The holder may include or may be shaped for example as a rod or stick, or tube, or pipe, or pole, for example a single or double rod or fork configured to be inserted into the soil. The housing further comprises a radio link characterization unit including for example a VNA (Vector Network Analyzer) and a transmit/receive subsystem. The radio link characterization unit is configured to transmit one or more radio signals from at least one of the antennas of the plurality of antennas and receive one or more propagated radio signals (e.g. reflected radio signals) from at least one of the antennas of the plurality of antennas for example by the transmitting antenna to yield a plurality of radio links. The system further comprises one or more processing units for converting the radio links characteristics into soil properties characteristics.

According to another embodiment the system comprises one or more antenna or sensor arrays for example an antenna arrays. An antenna array comprises a plurality of transmitting antennas for generating RF signals in the soil and a plurality of receiving antennas (e.g. receiving antenna array or sensor array) for receiving the RF signals. The one or more processing units are configured to analyze the RF propagated (or reflected) signals and measure the electromagnetic propagation characteristic of a path between the antennas for example between each pair of antennas in the array (e.g. between a transmitting antenna and a receiving antenna). For example, in a scenario including a single Tx antenna and 3 Rx antennas 3 pairs of antennas having 3 distinctive paths will be provided to provide a spatial distribution of the soil moisture and soil salinity.

In an embodiment the system is configured to instantaneously measure the soil moisture and/or salinity at various depths within the soil.

In an embodiment, the system is capable to provide data (e.g. spatial distribution of the soil moisture and soil salinity) within a fraction of a second, thus allowing to use it in a closed loop irrigation system.

Advantageously, embodiments of the invention do not require a tight or galvanic contact with the soil as required by prior art sensors. Whereas prior art sensors based on technologies such as capacitance or conductance sensors operate at low frequencies where electrons are transferred from the sensor to the soil. Specifically, in sensors provided by the prior art, the metallic part of the sensor must be kept in direct, galvanic and low resistivity contact with the soil. These requirements are sometimes difficult and sometime impossible to achieve in practice, as soil moves and turbulences constantly, especially when intensive irrigation is involved.

In other words, there is provided a soil measuring device and system which do not require any interaction of electrons with the soil. The indirect interaction with the soil according to the present invention is achieved by generating electromagnetic fields thus, eliminating the need for a tight contact between the sensor system and the soil.

Additionally prior art sensors use metallic parts that must be constantly in direct contact with the soil. As the soil is irrigated constantly this may cause the metal parts to become rusty over time. The antennas of the present invention may be covered with a plastic shield protector (e.g. radome) which is not susceptible to corrosion effects. Therefore there are no metallic parts in contact with the soil.

Embodiments of the invention provide an array of individual elements organized in a pre-defined order. For example, a sensor array comprising N antennas, will include M different paths between the N antennas where M is:

M=0.5*N*(N−1). By measuring some or all or most of the M paths, one can calculate in high accuracy the soil characteristic in the volume occupied between the antennas. The antennas may be arranged in multiple and various orders, schemes and locations.

Reference is now made to FIG. 1 illustrating a system 100 for measuring or characterizing soil, e.g. moisture and/or salinity, according to one embodiment. The system 100 comprises a probe, for example a base or holder part 110 connected to a housing unit 115, the housing configured to be easily completely or partially inserted into the soil 105. The housing unit 115 may be or may include a single or double rod or stick or pole part which may be inserted or may be buried in the ground. In an embodiment housing 115 may be fork-shaped. For example the holder 110 may be connected to one or two rods shaped as tent-pegs.

In an embodiment, the probe may be shaped as a cylinder such as pipe or rod sharpened at one end (e.g. sharpened ends 125 and 135).

In an embodiment, the housing 115 may include two rods such a first rod 120 and a second rod 130 connected vertically at one side (e.g. the flat side) of the holder 110 and in the other side (e.g. the sharp side) are inserted into the soil 105. The system further comprises an antenna array 140 comprising for example N antennas attached for example to rods 120 and 130. The antennas may be equally divided to two groups of antennas, group A (e.g. antenna array 150) and group B (e.g. antenna array 160), attached for example to two opposite sides of the holder 110, where N/2 antennas (group A) may be attached to rod 120 and N/2 antennas (group B) may be attached to rod 130. For example the system may include N=12 antennas where the first group of antennas A (150) includes six antennas 1A to 6A attached to the first rod 120 and a second group of antennas B (160) includes six antennas 1B to 6B attached to the second rod 130.

As shown in FIG. 1, rods 120 and 130 may be inserted into the soil 105 so antenna array 140 is buried in the soil while the holder part 110 may stand above the soil. The holder 110 may be marked or may include a reflector or any other visible part to enable the farmer to easily find the device and prevent powerful motor vehicles such as the farmer tractor or other machines crash the device.

It should be noted that by way of a non-limiting example only, the system 100 illustrated herein is fork or pitchfork shaped. It is understood that embodiments of the present invention may use any other kind of structure for inserting the system into the soil.

In an embodiment the rods 120 and 130 length may be 5, 6, 7, 8, 9, 10, 15, 20, 25, 30, 35, 40, 45, 50.55, 60, 65, 70, 75, 80, 85, 90, 95, 100, 105, 110, 115, 120, 125, 130, 135, 140, 145, 150, 155, 160, 165, 170, 175, 180, 190 or 200 cm long and a diameter of 1, 2, 3, 4, 5, 6, 7, 8, 9, 10, 15, 20, 25, 30, 35, 40, 45, or 50 cm.

In an embodiments the device or the electrical components of the device may be covered by a protection seal made of any electromagnetic transparent material, for example plastics e.g. ABS, PVC, Polyethylene, Polypropylene, PTFE (Polytetrafluoroethylene).

The system 100 further comprises an electronic and communication unit 170 housed for example within the holder part 110 of the system or in a rigid mechanical cover within the system. The electronic and communication unit 170 comprises one or more processors for example a processing unit 172 for processing the measured signals and characterising the soil and a transmit/receive subsystem 175 and a communication module 178, as will be explained in greater detail below.

For example the system 100 may be in wireless communication with a cloud based server or storage system. The communication unit 102 can acquire the data as described herein. The system can transmit the data with communication circuitry with a communication link, such as a wireless serial communication link, for example Bluetooth™. The hand held device can receive the data from the spectrometer 102 and transmit the data to the cloud based storage system. The data can be processed and analyzed by the cloud based server, and transmitted back to the system to be displayed to the user.

In an embodiment, the data is transmitted, for example wirelessly, by the communication unit 178 to a control center for further analysis and/or to provide farmers with relevant information to manage efficiently their irrigation systems. In some cases the control center may be included in the system 100 or external to the system.

In many embodiments, the system provides a user interface (UI) for controlling the operation of the device and/or viewing data as described in further detail herein.

In many embodiments, one or more of the system and cloud based server of the system may comprise a computer system configured to regulate various aspects of data acquisition, transfer, analysis, storage, and/or display. The computer system typically comprises a central processing unit (also "processor" herein), a memory, and a communication interface (also "communication circuitry" herein). The processor can execute a sequence of machine-readable instructions, which can be embodied in a program or software. The instructions may be stored in a memory location. Each device of the spectrometer system may communicate with one or more of the other devices of the system via the communication interface.

The transmit/receive subsystem 175 is configured to generate and transmit the RF signals, for example, from 10 MHz to 10 GHz, to a Radio Frequency Signals Measurement Unit (RFSMU) 179 such as a Vector Network Analyzer (VNA) for measuring the received/reflected signals, a data acquisition subsystem 180 and further a processing unit 172 (e.g. at least one electronic processing unit) for processing the measured signals and characterising the soil.

The transmit/receive subsystem 175 is responsible for generation of the RF signals, coupling them to the antennas, reception of the RF signals from the antennas and converting them into a form suitable for acquisition. The signals can be pulse signals, stepped-frequency signals, chirp signals and the like. The generation circuitry can involve oscillators, synthesizers, mixers, or it can be based on pulse oriented circuits such as logic gates or step-recovery diodes. The conversion process can include down conversion, sampling, and the like. The conversion process typically includes averaging in the form of low-pass filtering, to improve the signal-to-noise ratios and to allow for lower sampling rates.

According to some embodiments of the invention, the transmit/receive subsystem 175 may perform transmission and reception with multiple antennas at a time or select one transmit and one receive antenna at a time, according to a tradeoff between complexity and acquisition time.

The data acquisition subsystem 180 collects and digitizes the signals from the transmit/receive subsystem 175 while tagging the signals according to the antenna combination used and the time at which the signals were collected. The data acquisition subsystem 180 will typically include analog-to-digital (A/D) converters and data buffers, but it may include additional functions such as signal averaging, correlation of waveforms with templates or converting signals between frequency and time domain.

The processing unit 172 (e.g. at least one electronic processing unit) is responsible for converting the collected signals into responses characterizing the soil, and converting the sets of responses, into data relating to the soil characteristics as will be described in details hereinbelow. The processing unit 172 is usually implemented as a high-performance computing platform, based either on dedicated Digital Signal Processing (DSP) units, general purpose CPUs, or, according to newer trends, Graphical Processing Units (GPU).

In operation, each or some of the 6 antennas in the left side of the system (e.g. antennas 1A-6A) may transmit an RF signal to form a number of radio links paths with each of the 6 antennas in the right side of the fork (e.g. antennas 1B-6B). For example, in a system including N=12 antennas N/2×N/2 (6*6=36) 36 radio link paths are formed between the 'A' group and 'B' group antennas. At the next step the amplitude and phase of the radio links are constantly measured by the transmit/receive subsystem 175. In an embodiment, the measurement is carried over a wide bandwidth in the microwave frequency range typically 1, 2, 3, 4, 5, 6, 7, 8, 9, 10, 11, 12, 13, 14, 15, 16, 17, 18, 19, 20 GHz, or at any sub-band in this range.

At the next step, the measured amplitude and phase data of the 36 paths are converted by the processor 172 to soil properties as moisture and salinity in the volume surrounding the antenna array.

In some embodiments, the conversion may include a calculation according to amplitude and phase model as illustrated herein below.

For example, a model relating the amplitude/phase to the moisture/salinity, may be expressed as generalized series of polynomials according to the following Eq:

$$S=k0+k1*A+k2*A^2+k3*A^3+\ldots j0+j1*P+j2*P^2+j3*P^3+\ldots$$

$$M=m0+m1*A+m2*A^2+m3*A^3+\ldots n0+n1*P+n2*P^2+n3*P^3+\ldots$$

Where:
S=Salinity
M=Moisture
A=Amplitude
P=Phase and where k, j, m, n are complex constant numbers with known values, specific for a certain sensor design or a specific sensor part number.

In some embodiments the conversion may be according to a look up table which includes prior sensor calibration measurements.

For example, considering the path between each pair of antennas as a straight line, the soil would be sampled within a spheroid having its main axis aligned with the straight line. The lateral boundaries of the spheroid depend on the frequency used and the length of the line. In one embodiment which includes using microwave frequencies the dimensions of the spheroid lateral diameter may be around 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 33, 34, 35, 36, 37, 38, 39, 40, 41, 42, 43, 44, 45, 46, 47, 48, 49, 50 cm. and the data may relate to soil which is in proximity to the antennas.

Figure 2A:
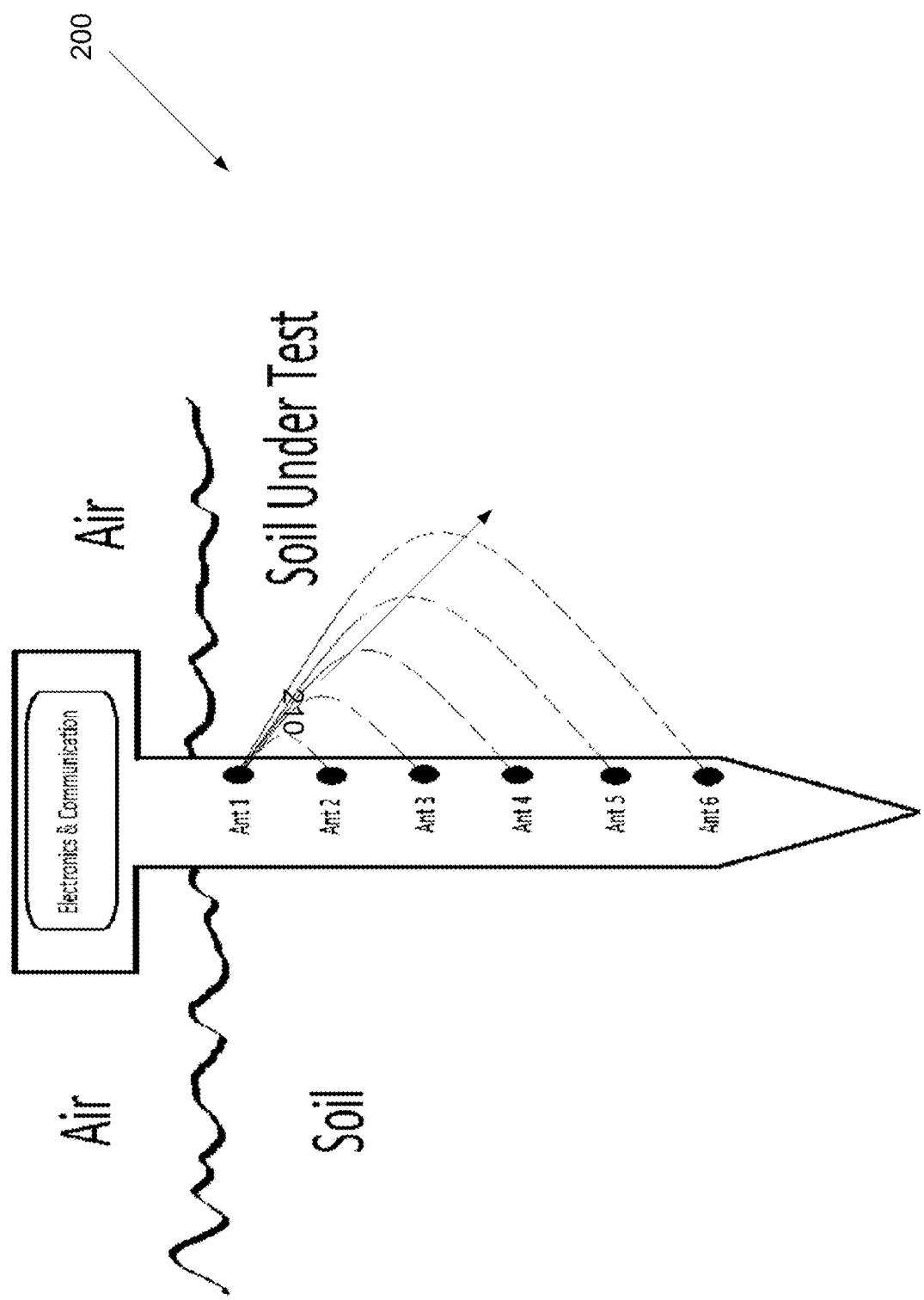
FIG. 2A is a diagram illustrating an alternative measuring system, in accordance with examples.

Reference is now made to FIG. 2A illustrating a device 200 according to another embodiment of the invention. Device 200 present all elements of aforementioned system 100 but instead of a double rod/fork shaped device, the device 200 comprises a single elongated rod or pipe structure for enabling a swift and easy insertion of the device 200 into the soil. An antenna array such a linear antenna array 210 is mounted along the rod, the antenna array 210 comprises N antennas mounted along the rod. In an embodiment the antenna array 210 may comprise N=6 antennas forming 0.5*N*(N−1) different paths through the soil.

Figure 2B:
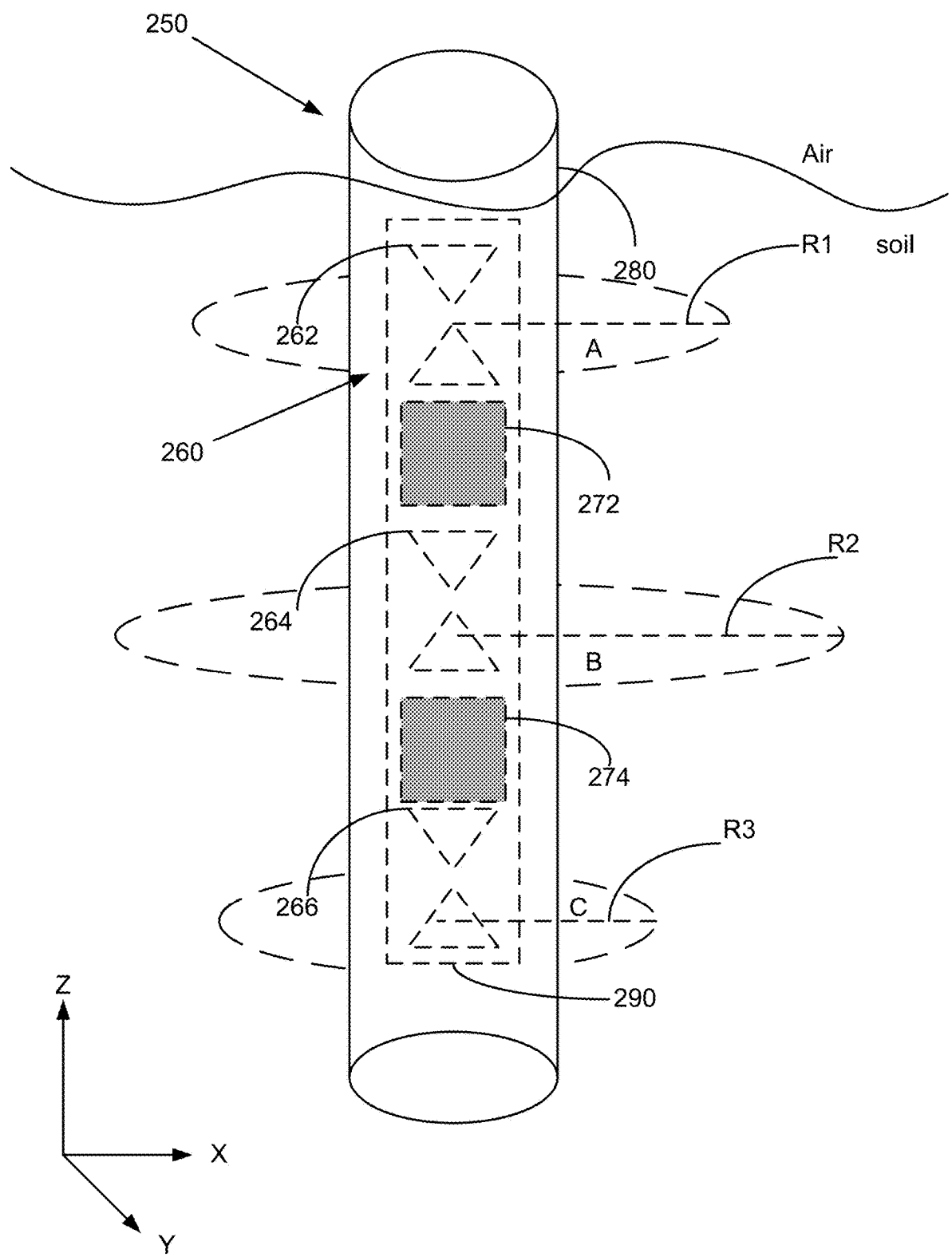
FIG. 2B is a diagram illustrating another embodiment of a device for characterizing the soil, in accordance with examples.

FIG. 2B illustrates another embodiment of a device 250 for characterizing the soil (e.g. sensing or measuring the soil content) for example soil surrounding the device. The device 250 may include a co-linear array of antennas 260, for example three dipole antennas 262, 264 and 266. In some cases the device may include more than three antennas for example 4, 5, 6, 7, 8, 9, 10, 11, 12, 13, 14, 15, 16, 17, 18, 19, 20 or more antennas.

In some embodiments one or more absorbing materials or objects such as absorbing materials 272 and 274 may be placed between adjacent antennas. The absorbing material is configured to minimize the mutual coupling between the antennas. The absorbing materials may be made of or include for example carbon or metallic particles embedded inside a foam or solid plastic.

The electronic components of the device such as the antenna array may be mounted on an electronic board, for example on a PCB 290. In some embodiments the antennas and the absorbing materials are placed within a pipe or tube for example in elongated pipe 280. The pipe may be made of plastic for example ABS, PVC, Polyethylene, Polypropylene, PTFE (Polytetrafluoroethylene) etc. or other materials configured to protect the device' electrical components.

The pipe dimensions may have a diameter of 1-1000 mm.

The reflection coefficient of each antenna is directly affected by the soil moisture surrounding the antenna, thru the soil dielectric constant.

A soil with higher moisture level will result in a material with a higher dielectric constant, accordingly areas along axis Z within the soil will be marked as 'wet or 'dry' areas. For example a soil status profile of areas (e.g. circles) A, B, and C may be measured accordingly by antennas 262, 264 and 266 and the radius R1, R2 and R3 of each area in an X-Y plane along Z axis may be calculated and provided to the user.

Figure 2C:
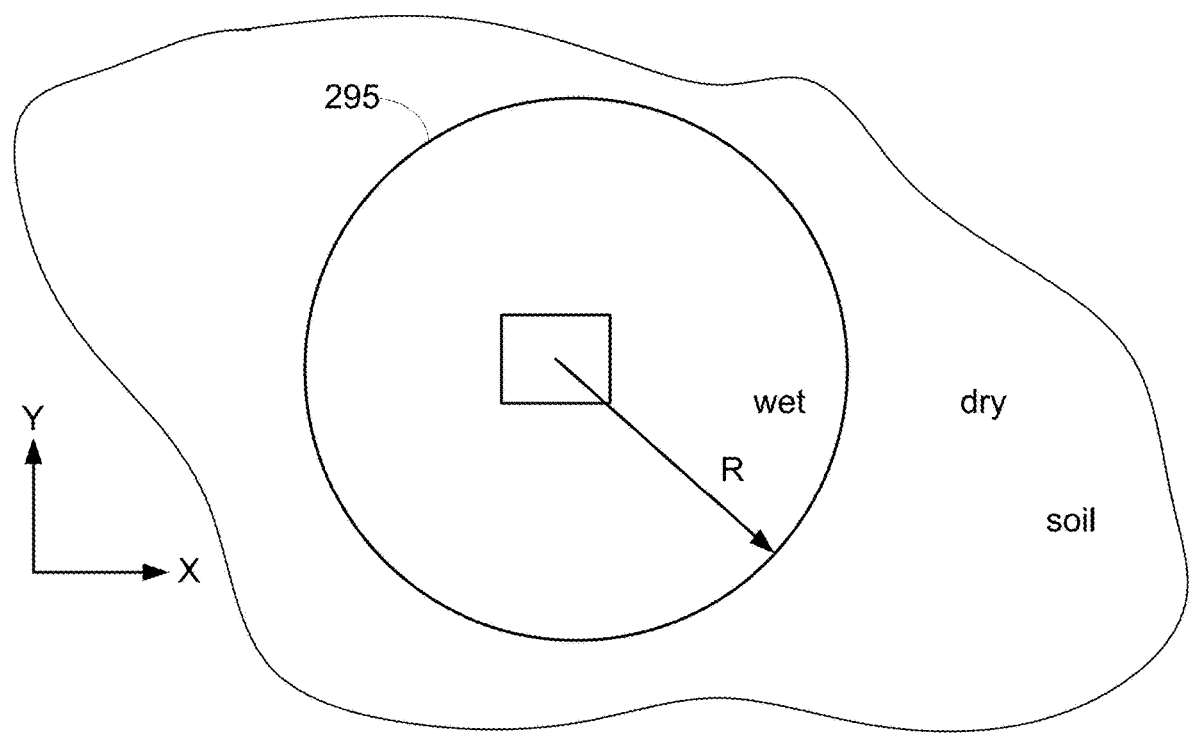
FIG. 2C is an upper view of a soil status profile, in accordance with examples.
Figure 2D:
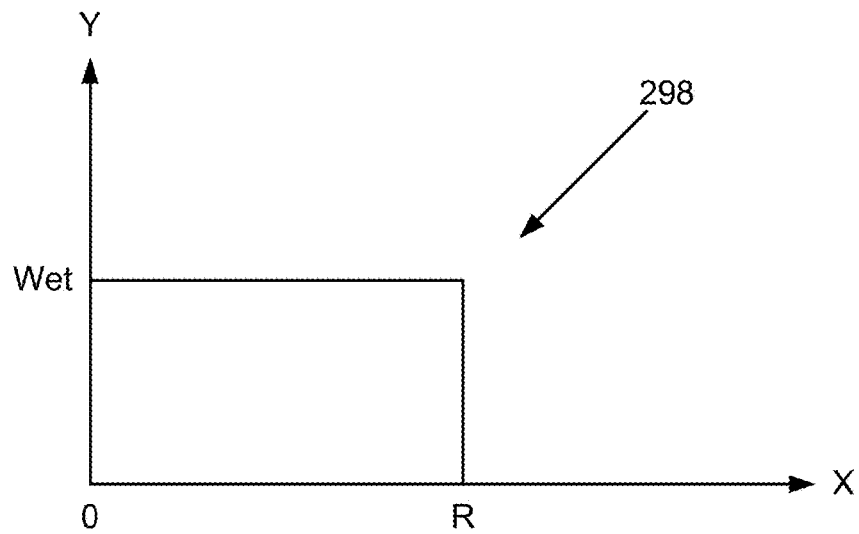
FIG. 2D shows exemplary graph of a soil status profile, in accordance with examples.

FIG. 2C is an upper view of a soil status profile, for example a soil's moisture status in accordance with embodiments. The wet area of the soil in a specific depth may be in the margins of circle 295 having a radius R and the dry area may be external to the circle 295. FIG. 2D is a graph 298 illustrating the soil moisture profile in an X-Y plane.

In some cases the soil status profile may be asymmetry having other shapes. It should be stressed that the accurate calculation measurement of the soil moisture and salinity profile versus the soil depth results from the numerous number of electromagnetic paths (some of them partially overlapping one another) formed between in the antenna array and the surrounding soil.

Figure 3:
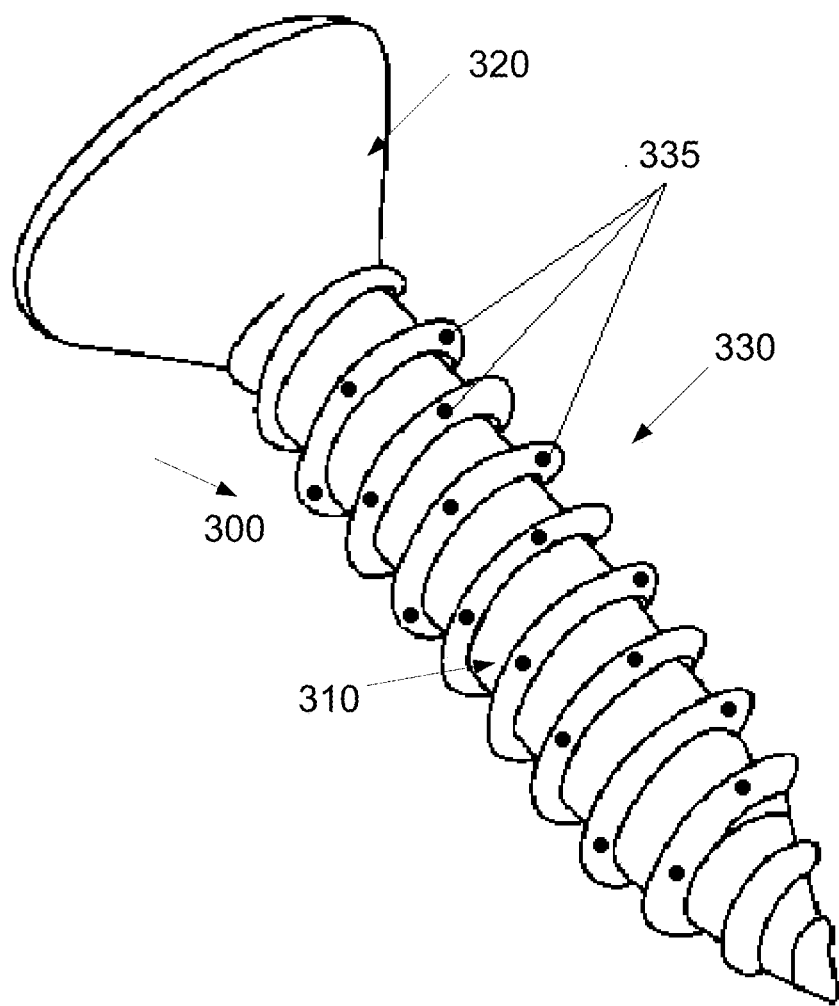
FIG. 3 is a diagram illustrating a screw shaped device, in accordance with examples.

Reference is now made to FIG. 3 illustrating a device 300 for measuring soil moisture and/or salinity, according to another embodiment. Device 300 is screw or bolt shaped comprising a helical ridge part 310, e.g. a thread wrapped around a cylinder configured to be easily inserted into the soil and a head part 320 at the end of the device which contains a specially formed shape such as cone shape that allows it to stand out of the ground. An antenna array 330 comprising a number of antennas 335 is externally helically wrapped around the thread part providing a plurality of electromagnetic paths between the antennas 335 of the antenna array.

Note, that unlike the rod-shaped array of device 200 (illustrated in FIGS. 2A-2B) in which the antennas are collocated along a straight line, in the screw-shaped array of device 300 the antenna array is positioned along a helical line.

As in the previous devices 100 and 200, each antenna or some of the antennas in the antenna array forms a radio link with all other antennas or some of the antennas, allowing an accurate measurement of the soil. The advantage of such an antenna arrangement is a result of the duality in the functions of the screw shaped device 300. On one hand the screw allows an easy installation of the device 300 into the ground, without digging or punching, and on the other hand it hosts the antennas in a helical arrangement. Such an arrangement allows each antenna to generate many radio links with the other antennas of the antenna array, similar to the rod and fork shaped devices.

FIG. 4 is a high level schematic block diagram illustrating system 400, according to some embodiments of the invention. System 400 may comprise an antenna array 410 configured to transmit and receive RF signals 402 to/from soil 405 such as soil surrounding the antenna array and a Vector Network Analyzer such as a Multi-Port Vector Network Analyzer (MPVNA) 420 for measuring a plurality of radio paths formed between each pair of antennas and the soil. The MPVNA 420 is configured to measure the amplitude and phase from each antenna to any other antenna in the antenna array e.g. the radio paths of the antennas. It is stressed that MPVNA 420 comprises at least the number of ports as the total number of antennas, for example for an antenna array comprising N=12 antennas a VNA comprising at least 12 antenna ports should be provided. In another embodiment the MPVNA may include a plurality of transmitter/receiver pairs, alternatively the MPVNA may include a single poll and a switching matrix.

The system further comprises at least one processor 430 (e.g. CPU) for receiving the radio data e.g. the amplitude and phase from the VNA and analyzing/converting the data to yield the soil moisture or soil salinity. The processor 430 may further provide a representation of soil information such as soil moisture or salinity vs. relative depth or distance of the soil from the antenna or according to an absolute depth of the soil. For example, the processor may provide information including soil moisture or soil salinity of a volume of 5 meters deep and 500 m square.

In some cases the processor may analyze the radio data e.g. the amplitude and phase of each antenna (e.g. antenna pair) at various locations and depths and provide spatial measurement of the soil's moisture or salinity pervasion profile as will be illustrated herein in respect to FIG. 2C.

The information may be transmitted wirelessly via communication module 440 to central unit such a municipal information or to a user electronic mobile device such as a farmer mobile phone or directly to an irrigation system for automatically controlling accordingly the irrigation system.

In an embodiment, the system 400 units may be energized via an internal power system 450. The power system may be configured to collect energy from the sun using solar panels and store electrical energy in the batteries for night time operation.

Figure 5A:
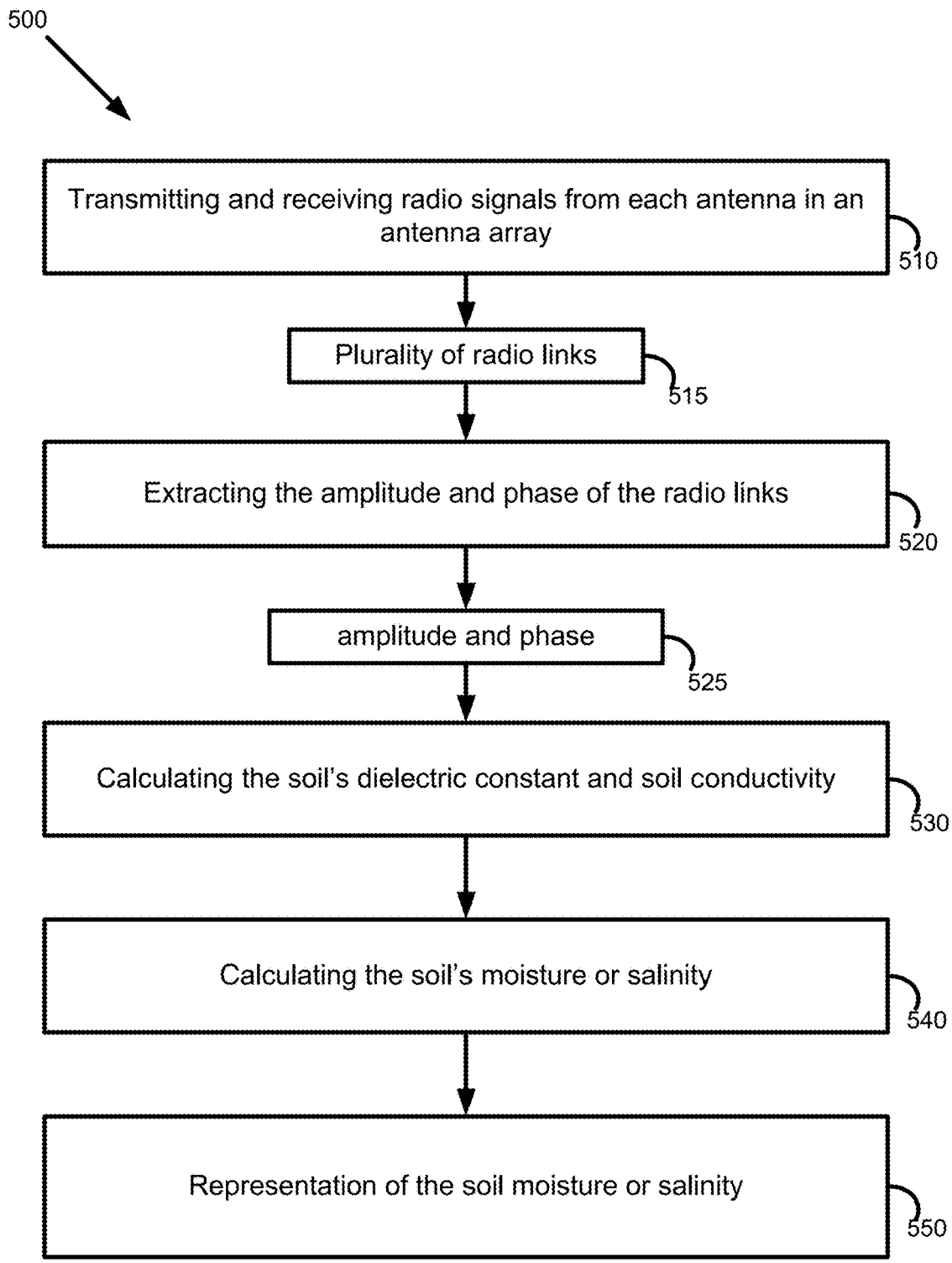
FIG. 5A is a high level schematic flowchart of method 500, in accordance with examples.

FIG. 5A is a schematic flowchart of method 500, according to some embodiments. Some stages of method 500 may be carried out at least partially by at least one computer processor (e.g., by processor 430 of FIG. 4 or processor 172 of FIG. 1). Respective computer program products may be provided, which comprise a computer readable storage medium having computer readable program embodied therewith and configured to carry out of the relevant stages of method 500.

Method 500 comprises transmitting and receiving radio signals from one or more antennas in an antenna array (step 510) to yield a plurality of radio links (515) between the antennas in the antenna array and the soil surrounding the antenna array. For example step 510 may include transmitting and receiving radio signals from each antenna in the antenna array.

According to some embodiments the transmitting antenna and the receiving antenna may be on different antenna arrays or rods or pipes. For example as shown in FIG. 1 the transmitting antenna may be on the first rod (e.g. antenna 1A of antenna array 150) and the receiving antenna may on the second rod (e.g. antenna 1B of antenna array 160).

In some embodiments, a radio signal may be transmitted and received by the same antenna array or the same antenna. For example, as shown in FIG. 2A a signal may be transmitted by antenna 1 of antenna array 210 and received by antenna 2 of the same antenna array.

The method further includes extracting the amplitude and phase (525) of the radio links (step 520), for example by the MPVNA 420 which is in communication with the antenna array.

Figure 5B:
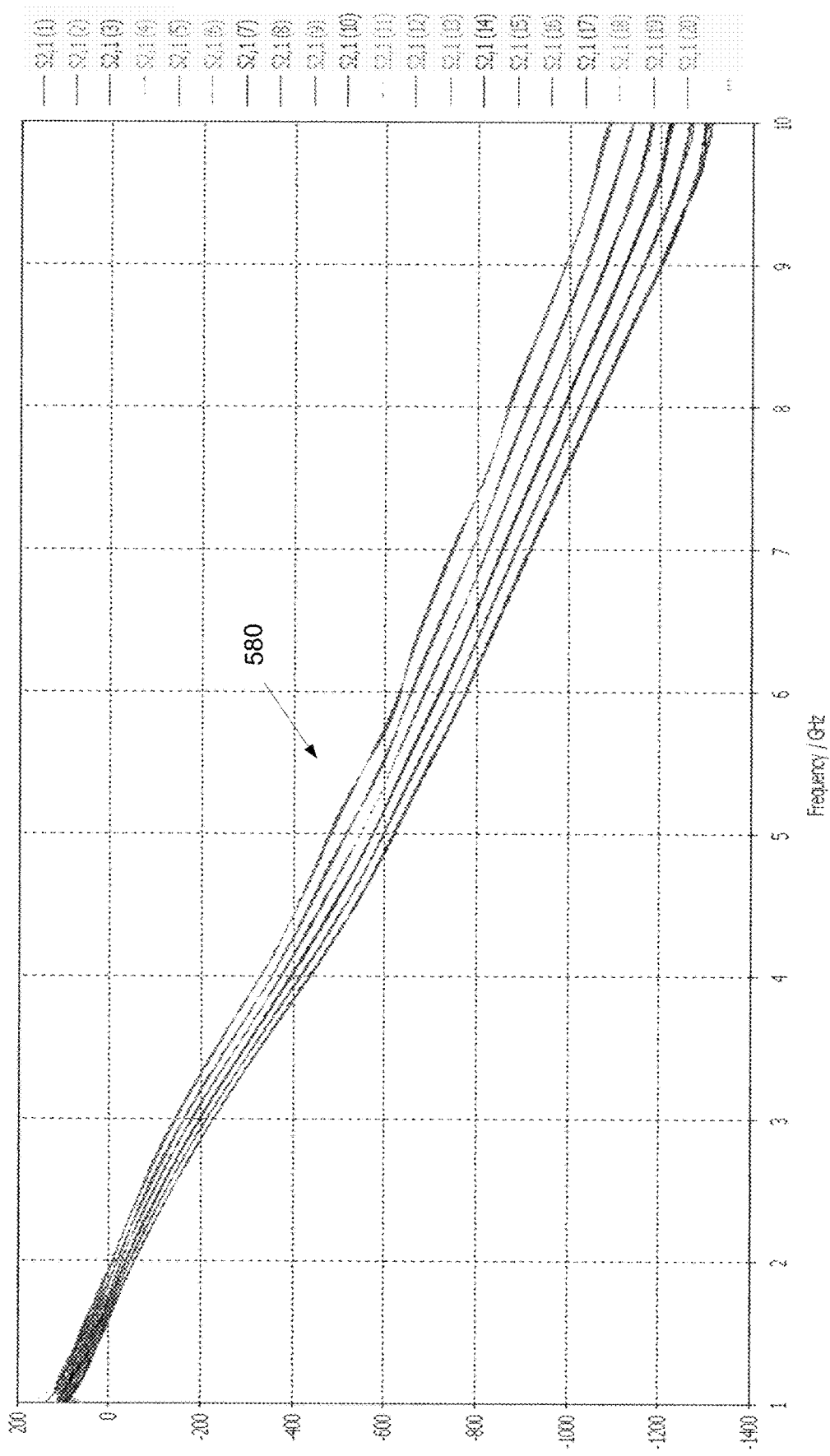
FIGS. 5B-5F illustrate a number of graphs representation of the radio links transmitted by the measuring device, in accordance with examples.
Figure 5C:
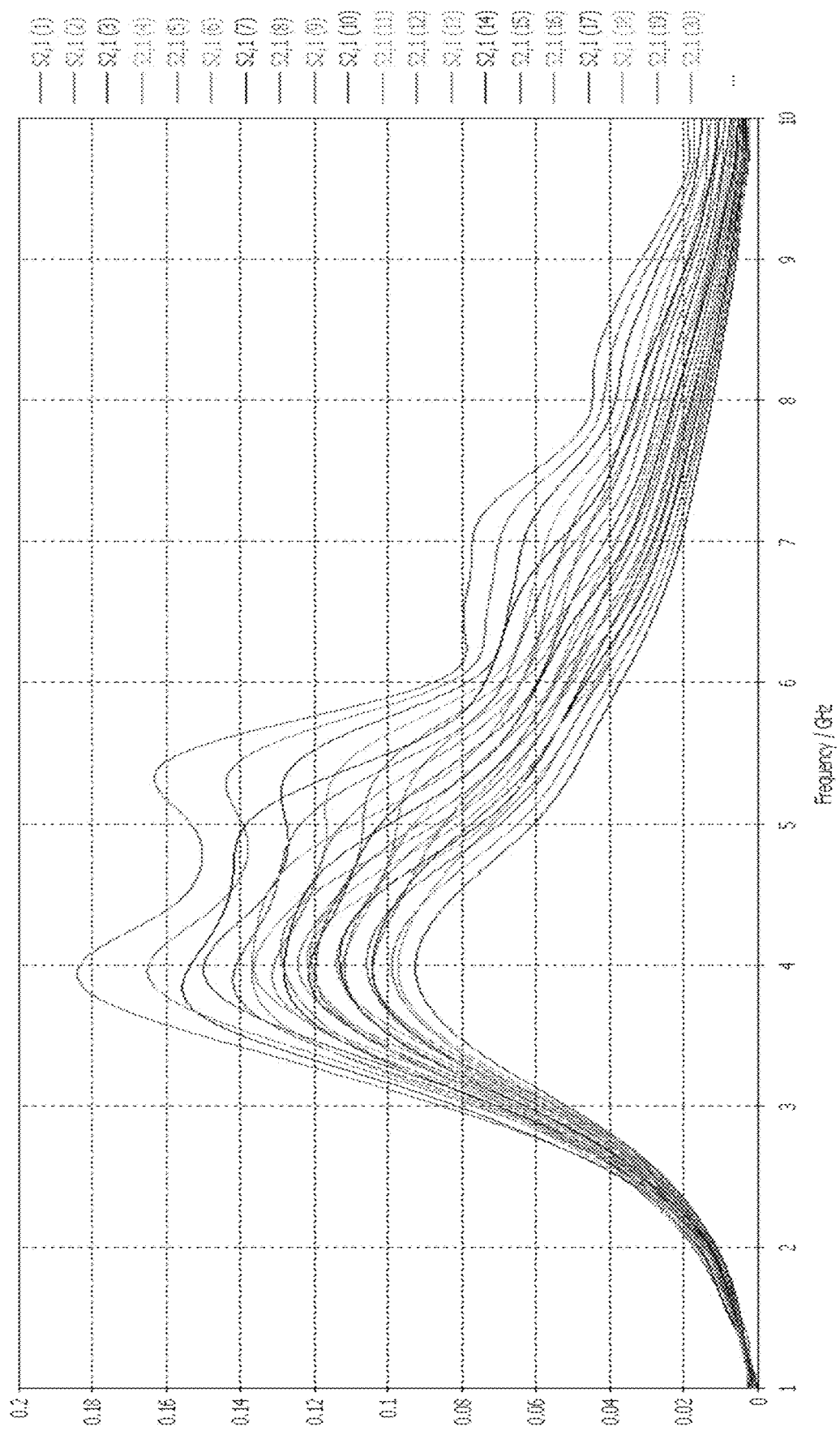

For example, FIGS. 5B and 5C illustrate an RF signal response of an antenna array such as the antenna array 140 of FIG. 1, according to embodiments. A representation of the radio links phase is illustrated by graph 590 of FIG. 5B while the amplitude is illustrated by graph 595 of FIG. 5C. The response illustrated by graph 580 (phase) and 590 (amplitude) is the transmission coefficient between one antennas' port to other antennas' port (S21), over frequency. The transmission response is shown for all 36 permutations created by 6 soil dielectric constant (Er'=5 to 10)) values and 6 values of soil DC conductivity ($\sigma$=0.01 to 0.2 s/m).

Figure 5D:
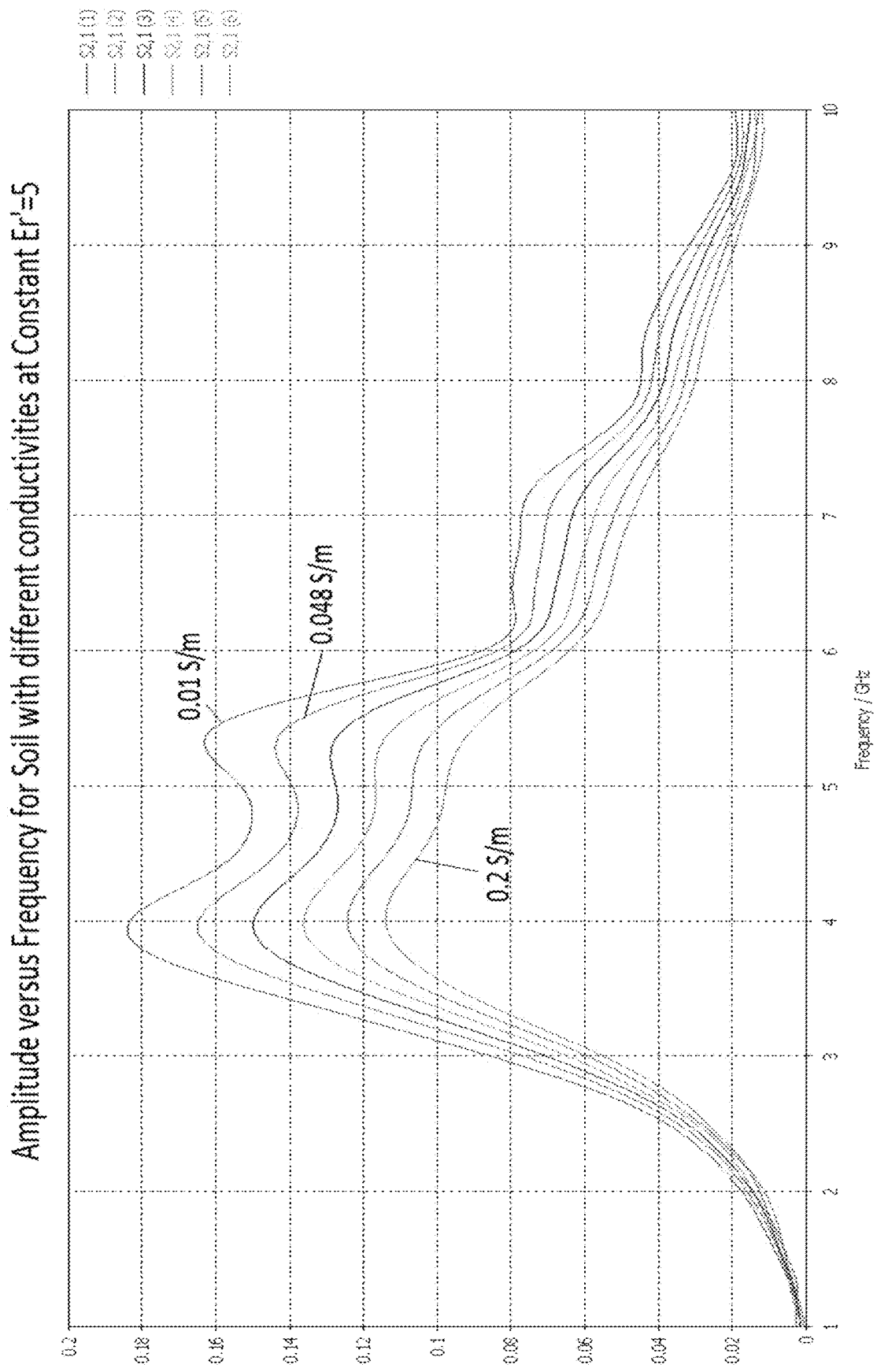
Figure 5E:
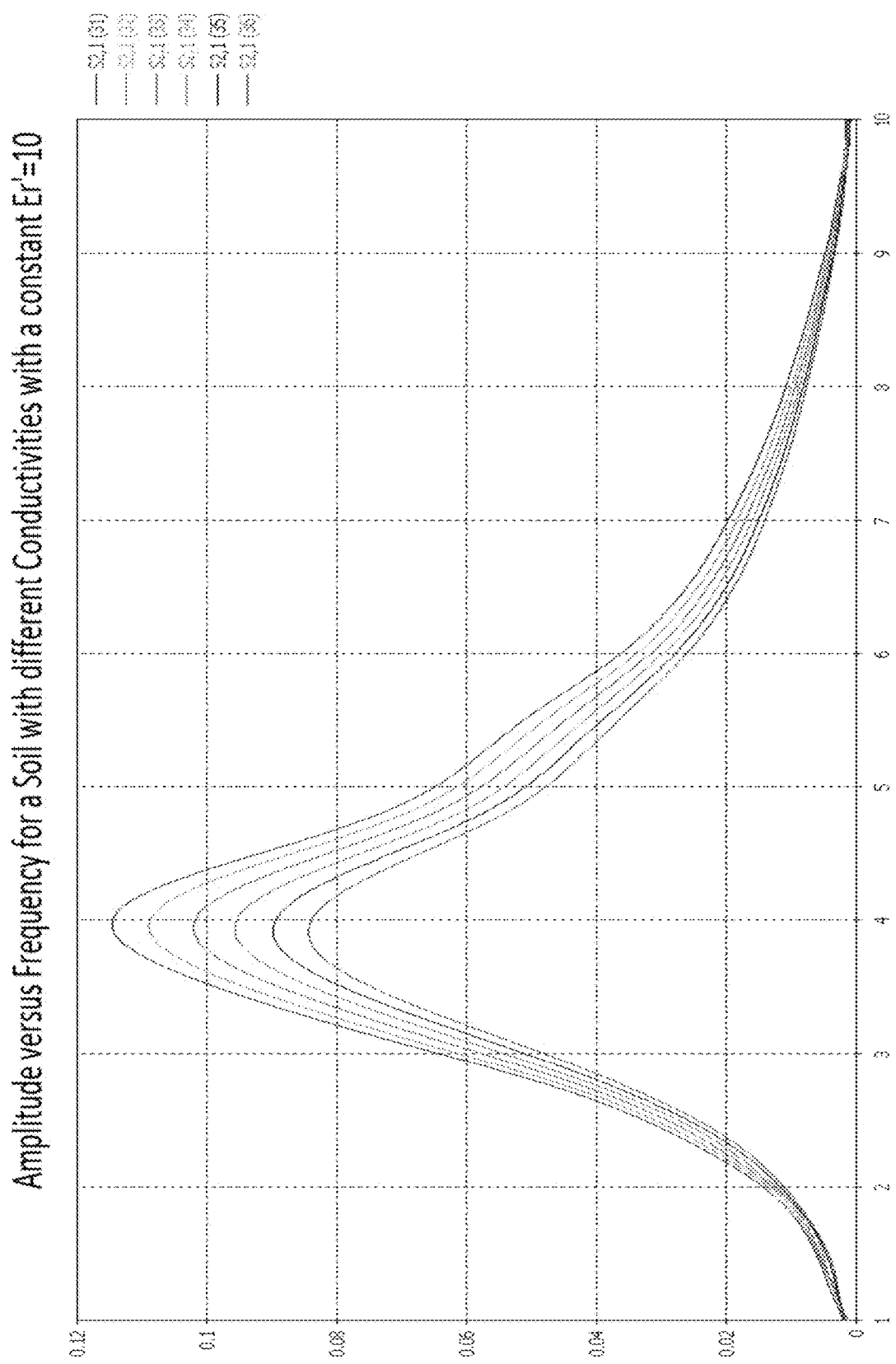

As shown in FIGS. 5B and 5C the phase is mainly influenced by the dielectric constant (Er'), and it is almost not sensitive at all to the conductivity (the 6 groups of lines correspond each to a different Er'). On the other hand the amplitude (FIG. 5C) is sensitive to both. A computational process is provided to extract the soil electrical parameters (Er',$\sigma$) from the measured response (S21 amplitude, S21 phase). One example of such a process will first extract Er' from the phase information, as illustrated in FIG. 5B. Each value of Er' is un-ambiguously associated with only a single response of the phase over the frequency, and it may be measure and correlated with a specific value of Er'. When Er' is already known, the conductivity may be un-ambiguously extracted from the amplitude response, as illustrated in FIG. 5D (Er'=constant=5) and FIG. 5E (Er'=constant=10). The sensor array response of S21 (amplitude and phase) versus frequency as a function of the soil electrical parameters (Er',$\sigma$) may be acquired by electromagnetic simulations, by direct calculations or by conducting a series of experiments with different soils having known parameters.

In some cases the method may include transmitting and receiving one or more RF signals from and by the same antenna, for example one or more signals may be transmitted from antennas 1, 2, 3, 4, 5 and 6 and received accordingly by the same antennas, e.g. transmitting from antenna 1 and receiving by the same antenna 1, etc.

The response illustrated by graph 598 is the transmission coefficient between the same antennas' ports (S11), over frequency.

Figure 5F:
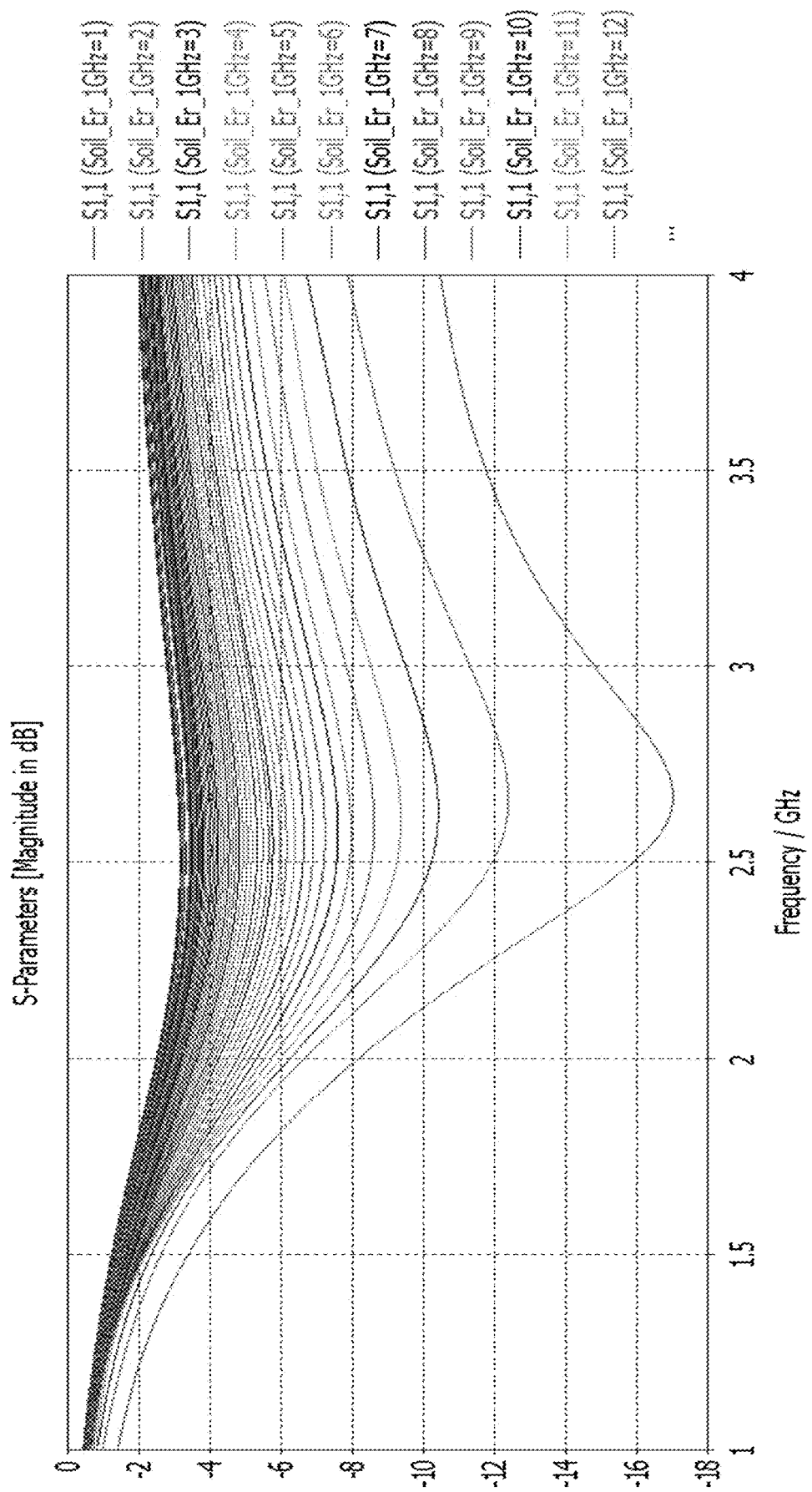

As shown in FIG. 5F a computational process may be provided to extract the soil electrical parameters (Er',σ) from the measured response (S11 amplitude, S11 phase).

The graph of FIG. 5F shows the antenna reflection coefficient is directly influence by the soil characteristic. The response is monotonic and simple. This allows to establish a reverse algorithm, that can accurately extract the soil moisture when the antenna reflection coefficient is known.

The next step (step 530) comprises calculating the soil's dielectric constant and soil conductivity (535) by a processor such as processor 430 to yield a representation of the soil content for example the soil moisture or salinity. At the next step (540) the soil moisture or salinity are calculated according to the computed soil's dielectric parameters (e.g. constant and conductivity). The conversion from soil's electrical parameters to moisture and salinity may be computed in some cases by a look-up table, prepared in advance. The table may be produced by measuring the soil electrical properties as a function of moisture and salinity. A different approach may avoid the intermediate stage of calculating the soil electrical parameters. Such an approach may be used in complex sensor systems where the transfer function correlating the inputs and outputs may not be known. In such a method the sensor array is exposed to multiple combinations of inputs (moisture/salinity), while the outputs (amplitude/phase) are measured and recorded. These forms known as a training set (or data base) for the sensor. When put to work in the field, any new output measured value is associated with the most probable input by employing regression analysis. Known regression analysis methods as linear regression or ordinary least squares are capable of producing accurate results in the case of the suggested sensor array, since the dependence between inputs and outputs is relatively simple.

According to some embodiments, a graphical user interface (GUI) presents data, e.g. soil properties characteristics results to a user (step 550), for example at the user's mobile device i.e. mobile phone, PC etc.

Figure 6A:
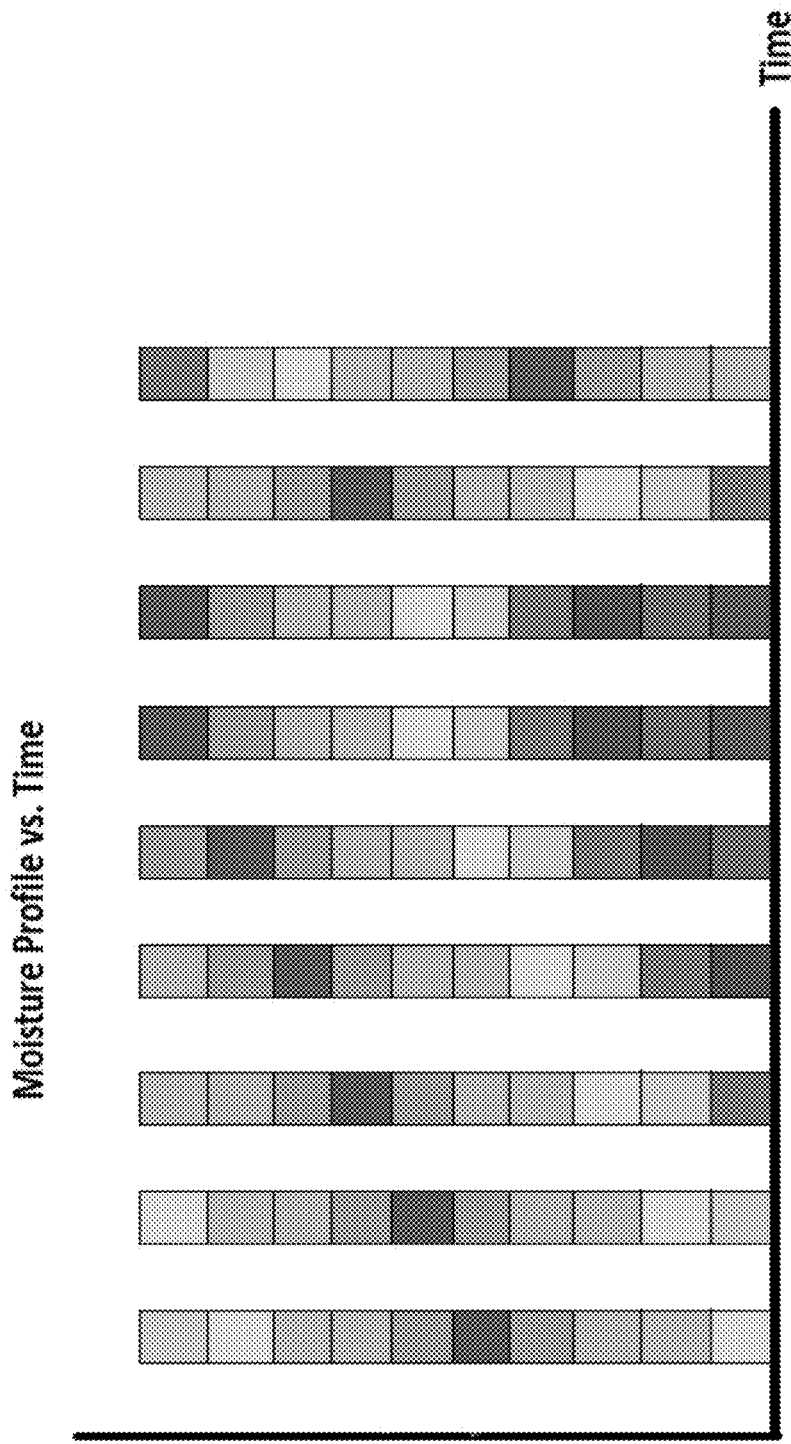
FIG. 6A illustrates a GUI comprising a plurality of blocks representing the moisture or salinity percentage profile in the soil, in accordance with examples.

FIG. 6A illustrates a GUI (graphical user interface) 600 comprising a plurality of colored blocks representing the moisture or salinity percentage profile in the soil at different depth levels where the X axis is time and Y axis is the depth of the soil and the colored gray scale blocks represent for example the moisture or salinity percentage level at a specific time and depth. It is stressed that other graphical representations may be used to illustrate the soil profile.

Figure 6B:
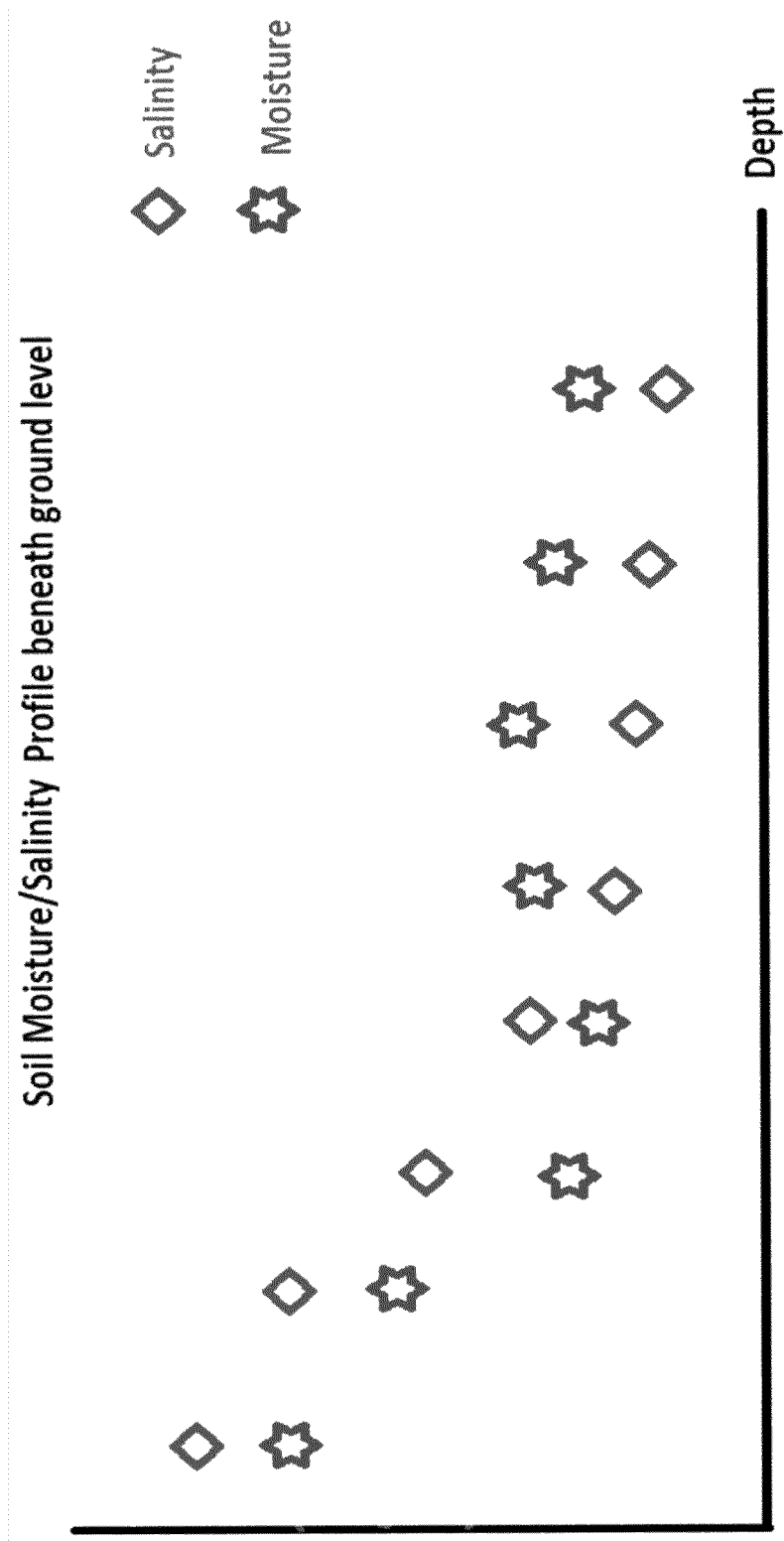
FIGS. 6B and 6C illustrate a GUI comprising moisture and salinity profile at the soil in constant depth over time, in accordance with examples.
Figure 6C:
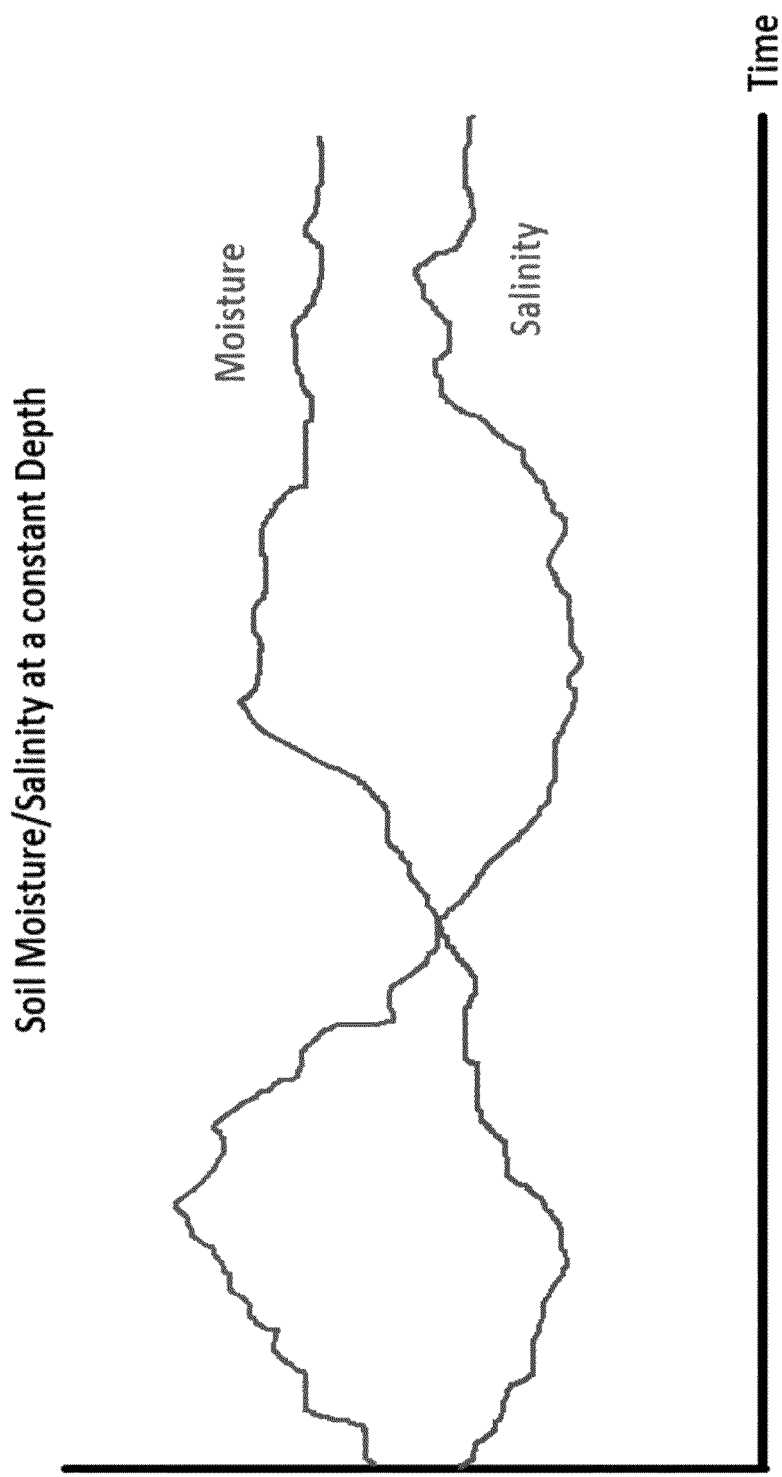

FIGS. 6B and 6C illustrate a GUI comprising moisture and salinity profile at the soil in constant depth over time, while FIG. 6A illustrate a GUI of moisture and salinity profile in the soil at different depth levels.

Based on such characteristic features as illustrated in the graphs of FIG. 6, an irrigation system as described herein may be managed efficiently, by comparing for example the measured soil profile status against previous soil profile measurement, as described herein.

It is stressed that the volume of soil that may be sensed in accordance with some embodiments depends on the dimension and structure of the antenna array and/or the antennas in the antenna array e.g. antennas size and distance of the antennas from one another etc. According to some embodiments there may be provided different types of systems and applications configured according to the soil or crop type, for example an antenna array adapted for Golf courses and an antenna system configured for corn crops. In some cases, the antenna system is set according to the irrigation depth of interest. For example for grass, as the roots depth are shallower than trees, accordingly the antenna array for trees would be longer (deeper) as the roots are larger.

Monitoring the Development of Plant's Root System/Plant Growth

Moisture analysis covers a variety of methods for measuring moisture content in both high level and trace amounts in solids, liquids, or gas. Moisture in percentage amounts is monitored specifically in commercial food production. There are many applications where trace moisture measurements are necessary for manufacturing and process quality assurance.

In accordance with embodiments of the invention there are provided methods and systems for monitoring the development status of a plant, for example the plant's root system over time in any type of soil (e.g. loam, clay, etc).

These methods comprise of obtaining a plurality of RF signals from one or more layers of a soil and processing the obtained signals by one or more processor units to yield the soil's moisture profile over time. Moisture is related to the phase response of a signal propagating through or reflecting from the soil. In particular, the moisture percentage affects the dielectric constant of the wet soil and changes the velocity of electromagnetic propagation.

An RF measuring system or device as described herein may be physically and/or functionally used to monitor and/or measure the development of an agricultural product such as plant (e.g. corn, bananas, avocado etc.). A system or device, in accordance with embodiments, comprises a plurality of transmitting antennas for generating RF signals in the soil and a plurality of receiving antennas for receiving the RF signals, and one or more processor units for monitoring the development of a product, such as a plant's root. In some instances the device or system may be the system shown in FIGS. 1-3, although other devices as known in the art may be used to monitor a product.

A number of experiments provided by the present invention applicant resulted in a very interesting correlation, indicating that the presence and amount of roots at given depth affects the rate of change of moisture at that level.

Figure 7A:
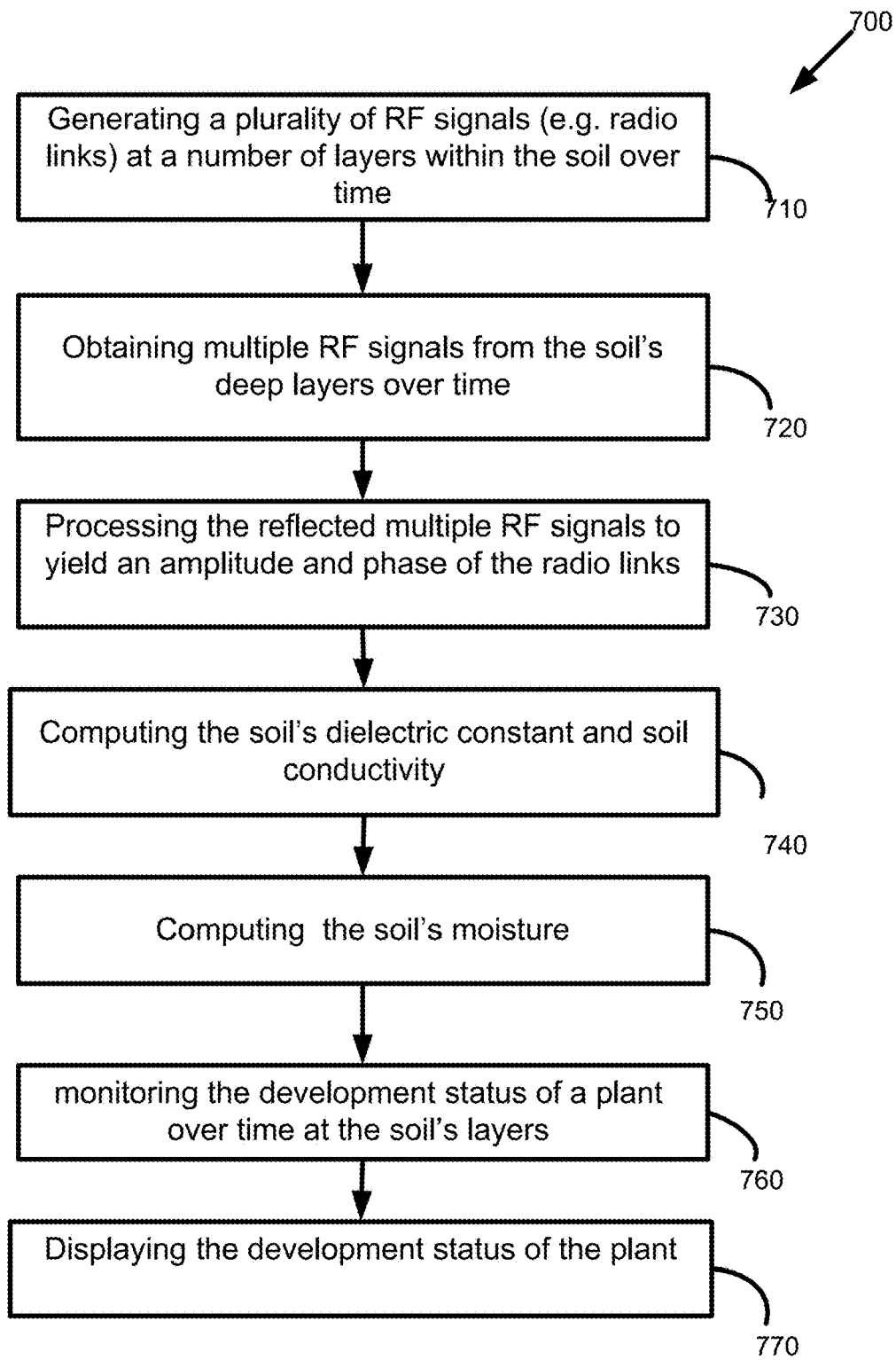
FIG. 7A shows a flowchart of a method for monitoring a development of a plant, in accordance with examples.

FIG. 7A shows a flowchart 700 of a method for monitoring a development of a plant, in accordance with embodiments. The method begins at step 710 which includes generating a plurality of RF signals (e.g. radio links) at a number of layers within the soil over time by an RF antenna array, including a plurality of antennas covered deep in the soil or in proximity to the soil surface. Step 720 includes obtaining multiple RF signals reflected from the soil's layers and step 730 includes processing the reflected multiple RF signals to yield an amplitude and phase of the radio links. Step 740 includes computing the soil's dielectric constant and soil conductivity followed by step 750 which includes computing the soil's moisture in each of the soil's deep layers.

Specifically, the soil's computation assumes that the dependence of moisture in time at a given layer, s(t), can be represented as an exponential function as follows:

$$s(t)=a*e^{(-t\tau)}+b$$

The amplitude and bias of this function are dependent on the amount of water in the irrigation therefore the decay rate t is only compared. At the next step the minimum of the moisture is removed and divided by the maximum:

$$f(t)=(s(t)-b)/a$$

And the following Eq is received:

$$f(t)=e^{(-t\tau)}$$

More specifically, in operation a device or system such as system 100 or 200 of FIG. 1A or 2A comprising one or more transmitter and receiver antennas at a specific layer at the housing part 115 are placed in the soil and data relating to the soil, such as moisture is extract from the phase response. Once the moisture behavior in time for a given layer is obtained, a processor such as processing unit 172 may compute the status of the plant growth in step 760, by monitoring the rate of change of moisture—τ, in the ground at different depths.

In some cases, the obtained information (e.g. plant growth status) may be further used for controlling a crop irrigation. For example the RF system such as system 100 or 200 may be in communication with a closed loop irrigation system, in operation the RF system may monitor the depth of the roots and control the amount of irrigation accordingly.

In some instances, the resulted moisture profile over time is processed to obtain a product, such as an agricultural product root status. For example a stepped frequency signal is transmitted at a range of for example 1, 2, 3, 4, 5 or 6 GHz and the moisture in the soil for example a loam soil comprising a plant for example corn is analyzed. The analysis may include measuring the plant's root system (e.g. corn root system) using the moisture time series in each layer.

Figure 7B:
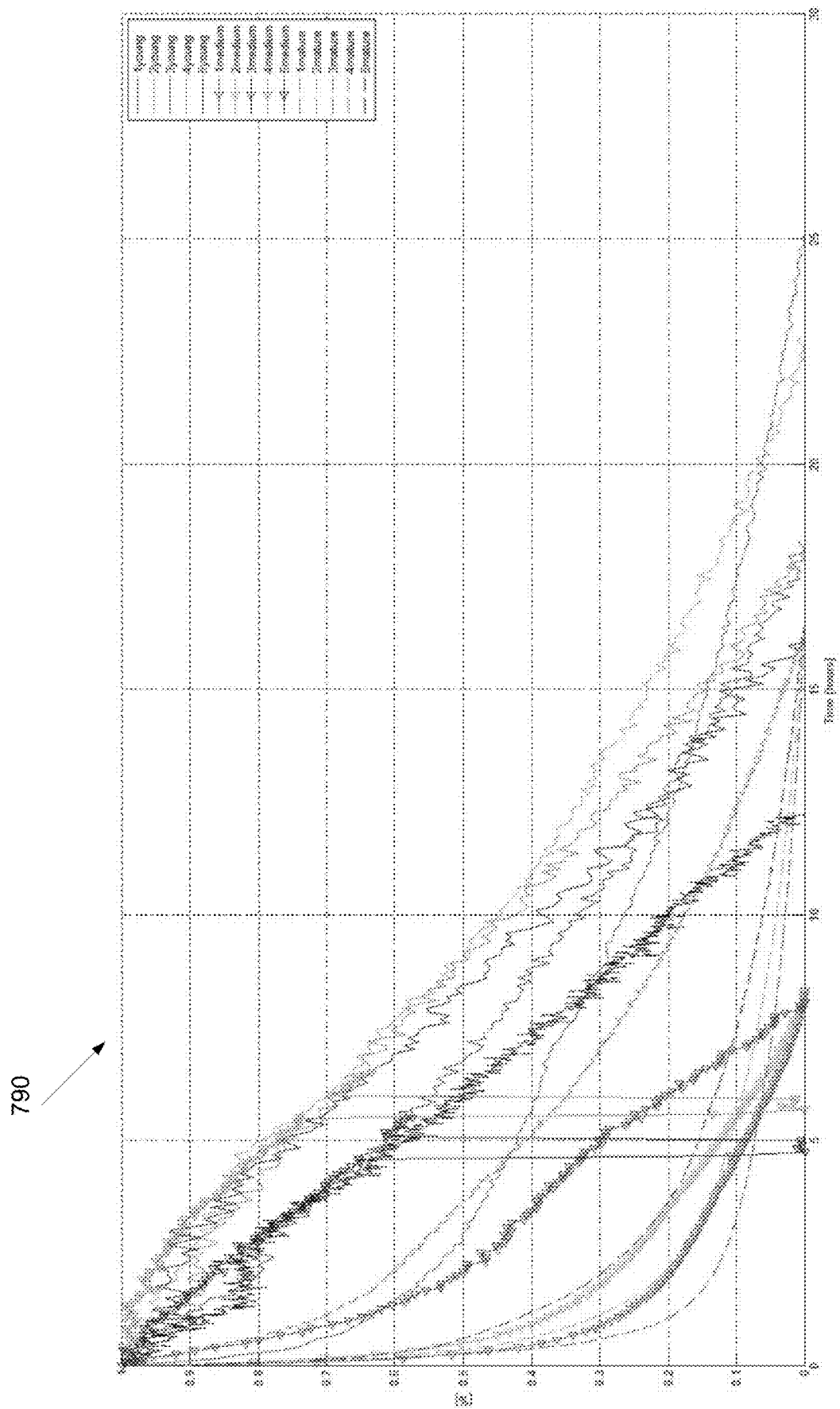
FIG. 7B shows exemplary graph of a resulted normalized function for each layer in the soil and respectively corn maturity over time, in accordance with examples.

FIG. 7B shows exemplary graph 790 of a resulted normalized function for each layer (in a different gray scale color) in the soil and respectively corn maturity (line style) over time, in accordance with embodiments. In some cases, the normalization is performed by obtaining a batch of moisture measurements of a specific layer which start with the peak of the moisture level and ends with minimum moisture level after absorption. This hatch is normalized by subtracting the minimum level of the moisture and dividing the result with the maximum level of the moisture as illustrated herein above. This process ensures that the normalized moisture time series is independent of the amount of irrigation. At the next step the normalized moisture time series as a decaying exponent and the decay exponent/rate is measured and estimated.

In an embodiment, the measured decay rate for each layer of the soil may be utilized to indicate the level of the roots system/growth of the plant. It is noted that in some cases as the root system of the crop such as corn is wide and varies considerably spatially, and sometime may only indicate the different water absorption properties in each layer, which are correlative with the crop evolution state.

Comparison of Corn Evolution

According to embodiments an analysis of graph 790 of FIG. 7B provides the following findings in respect to crop such as corn monitored by an RF system:

Higher absorption rate in more mature corn than in younger corn;

Similar absorption rate (e.g. decay rate) for the medium and mature corn in the upper layers. It was also indicated that above a specific layer of the soil the mature corn has a higher absorption rate. This also occurs for the medium corns versus the young corn. This effect can indicate the root level.

It was also found that the absorption in a given layer increases with the maturity of the corn—up to a certain layer—which may be related to the height or length of the roots.

An Array for Measuring Moisture Levels in Soil

According to some embodiments, a device for monitoring and/or measuring crop growth development such as corn moisture levels may include a device such as a sensor comprising one or more arrays, for example one or more antenna arrays. In some embodiments the device may include two columns of antennas as illustrated in FIG. 1.

Figure 8A:
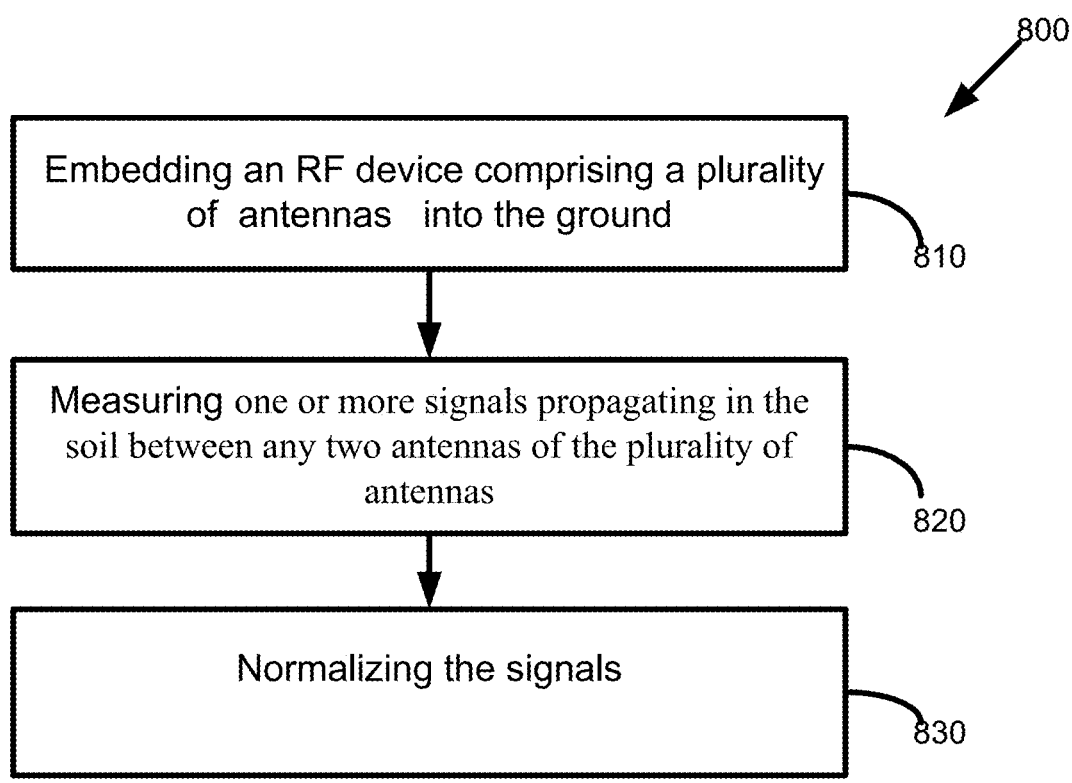
FIG. 8A shows a flowchart of a method for monitoring and/or measuring a development of plant's growth such as root system/plant growth, in accordance with examples.

A method for monitoring and/or measuring a development of plant's growth such as root system/plant growth, according to another embodiment, is described in FIG. 8A. In operation, the device is inserted into the ground (810) so that soil 190 covers and/or surrounds the antenna array for example at a gap 190 between the antennas. In some cases an area which may be measured may be between 1-50 cm, for example the gap 190 between the antenna arrays may be 27.5 mm. At the next step (820) one or more signals propagating in the soil between any two antennas is measured, for example the measurement may be activated by the processing unit 172. In some cases a reference channel may be used to remove the effect of the temperature on the frequency response of the cables connecting to the antennas. The reference channel may include two or more cables connected together or embedded in the soil. Examples In some cases, the measurement process includes mapping adjacent antennas of the antenna array to distant ports in order to reduce and/or eliminate the effect of leakage between adjacent ports.

At the next step (step 830) the signals (e.g. S21 or S11) are normalized using for example an air measurement (e.g. record and divide by air S21). This way some of the transfer function of the cables are calibrated. However, the change of dielectric substance between the two antennas also creates a different response than the air and may need further calibration.

Moisture Effect on the Phase Response

Figure 8B:
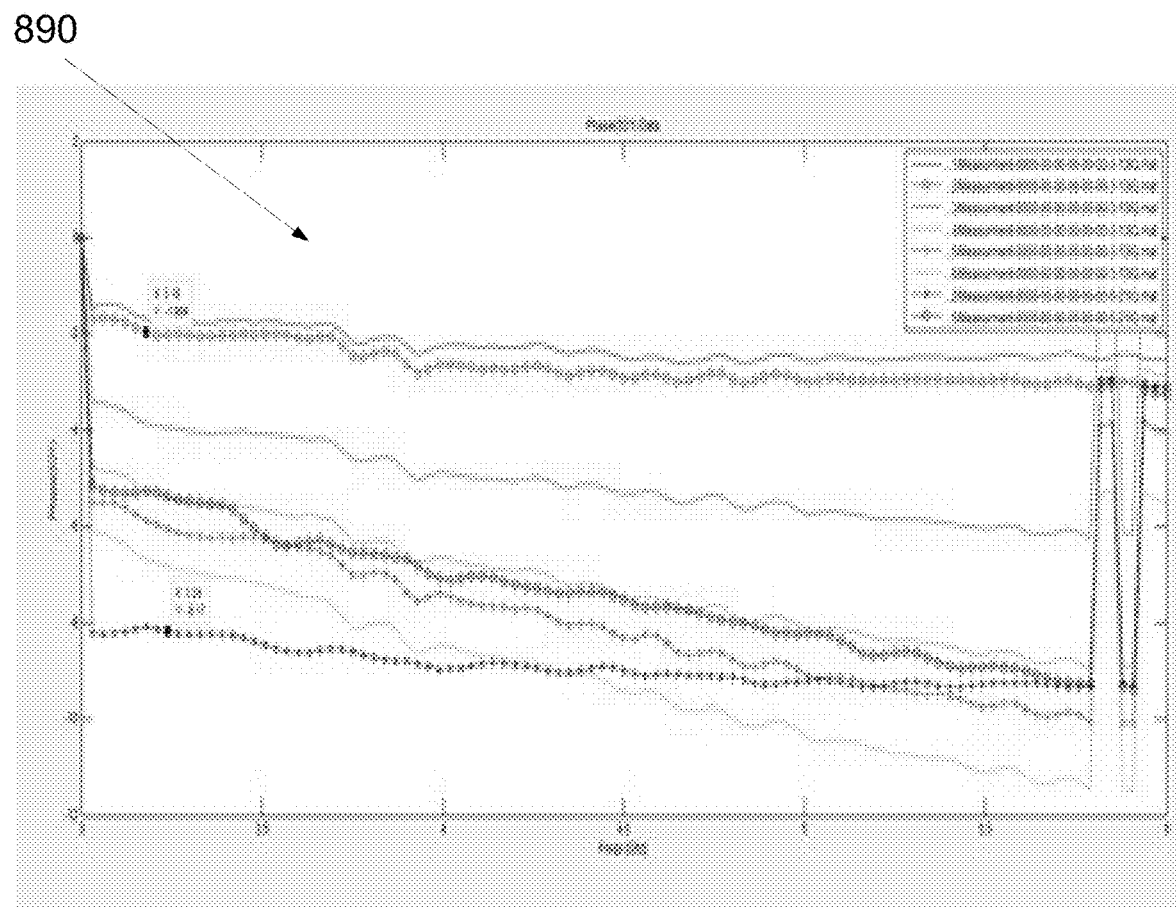
FIGS. 8B-8C illustrate exemplary graphs obtained from a number of soil samples with different moisture densities, in accordance with examples.

FIG. 8B illustrates a graph 890 obtained from a number of soil samples with different moisture densities. The graph 890 shows that there is a linear relation between the slope and moisture level. Additionally as illustrated by graph 890 there is a relation between the moisture level and the antenna phase response, e.g. as the moisture level increases, the negative slope of the phase response increases as well.

Figure 8C:
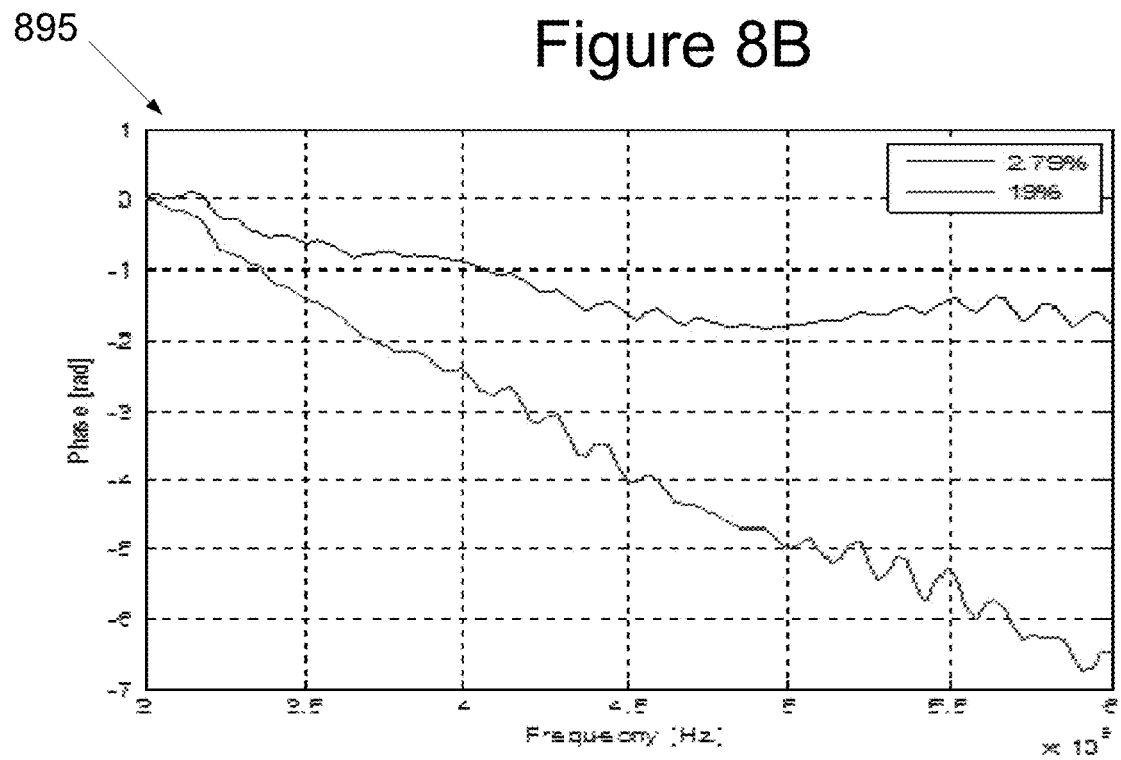

Specifically, at graph 895 of FIG. 8C the 2.79% moisture measurement doesn't behave like a linear line from around 4 GHz, while 19% moisture does. This can be due to the fact that the introduction of soil between the antennas creates a change of the soil response.

Phase Response Model

In some cases the phase response is normalized by recording the device phase response in air, dividing the signals in air and then inserting the device to the soil. If the device was embedded in dry soil, the phase response would change. The proposed model assumes that the dry soil creates an additive unknown non-random transfer function $\phi\_0\backslash(f\backslash)$ (which may be different for each link).

The phase of the recorded signal (S21 thru) is denoted as $\phi\backslash(\alpha, f\backslash)$ and it is assumed that it is a function only of the square root of the moisture density α and the frequency f. This function behaves according to the following model:

$$\phi\backslash(\alpha, f\backslash) = a\_0 + a\_1\sqrt{\alpha} + a\_2 f\sqrt{\alpha} + \phi\_0\backslash(f\backslash)$$

Where a_0, a_1 and a_2 are fixed coefficients which are constant for a set of TX-RX antennas and for a specific soil type. The phase response $\phi\_0$ (f) is the response to a given soil type per TX-RX link.

The square root dependency of the moisture is due to the fact that the velocity of a plane wave travelling through a homogenous medium is proportional to the square root of the dielectric constant and we assume a linear relation between the dielectric constant and the moisture.

Model Calibration

In some cases, the device and system according to embodiments may be calibrated by mixing a number of soil types such as loam mixed with tap water and NaCl (table salt) to obtain variable moisture and salinity levels. The different moisture levels are described in the table below.

| Sample ID | saliently level |
|---|---|
| soil 1 | 1.87% |
| soil 2 | 4.54% |
| soil 3 | 9.9% |
| soil 4 | 10.8% |
| soil 5 | 10.976% |
| soil 6 | 16.29% |
| soil 7 | 22.9% |
| soil 8 | 23.89% |
| soil 9 | 24.76% |

At the next step the measurements may be normalized by measuring air between the antennas and using this result as a reference normalization for next measurements in soil. At the following step an S21 signals were measured between for example 3 GHz to 6 GHz every 300 MHz (101 points).

Parameter Estimation

In some embodiments the parameters are estimated in a sub optimal manner. In order to reduce the number of parameters for estimation, the phase of the first frequency is subtracted from all or almost all the frequencies, thus centering the phase response and making it much easier to work with (less susceptible to wrap around issues and remove the model parameters which are not dependent on the frequency!)—$\phi^{\sim}\backslash(\alpha,f\backslash)$.

$$\phi^{\sim}\backslash(\alpha,f\backslash)=\phi\backslash(\alpha,f\backslash)-\phi\backslash(\alpha,f\_0\backslash)$$

$$\phi^{\sim}\backslash(\alpha,f\backslash)=a\_2(f-f\_0)\sqrt{\alpha}+\phi\_0\backslash(f\backslash)-\phi\_0(f\_0)$$

It is possible to estimate the parameter a_2 and the phase response $\phi\_0$ (f). First, we will run over all the possible combinations of two different moisture densities $\alpha\_1, \alpha\_2$ created in the lab (provided that they are different enough) and create a difference phase response per link—

$$\phi^{\sim}\backslash(\alpha\_1,f\backslash)-\phi^{\sim}\backslash(\alpha\_2,f\backslash)=a\_2(f-f\_0)\sqrt{(\alpha\_1)}+\phi\_0\backslash(f\backslash)-\phi\_0(f\_0)-(a\_2(f-f\_0)\sqrt{(\alpha\_2)}+\phi\_0\backslash(f\backslash)-\phi\_0(f\_0))$$

$$\phi^{\sim}\backslash(\alpha\_1,f\backslash)-\phi^{\sim}\backslash(\alpha\_2,f\backslash)=a\_2(f-f\_0)\backslash(\sqrt{(\alpha\_1)}-\sqrt{(\alpha\_2)}\backslash)$$

In this manner it is possible to estimate the model parameter a_2 using LS, given the knowledge of the two moisture levels $\alpha\_1, \alpha\_2$. The model parameter a_2 is estimated per link and averaged on all the possible combinations of measured moisture levels.

After estimating a_2 per link and averaging on different $\alpha\_1, \alpha\_2$, we estimate the centered $\phi\_0$ (f)(=$\phi\_0^{\sim}$) in the following manner, $$\phi\_0^{\sim}(f)=\phi^{\sim}\backslash(\alpha,f\backslash)-a\_2(f-f\_0)\sqrt{\alpha}$$

Now the moisture level for each link using the following equation is estimated:

$$\phi\_(\alpha\_w)(f)=\phi\_0(f)+2\pi f a\_2\sqrt{(\alpha\_w)}$$

$\sqrt{(\alpha\_w)}$ is computed using LS, take the power of two and then average using all the links associated with the specific layer (in our case it's all the links with the same Tx).

It is noted that a proper estimation using LS would compute also the bias of the phase response estimation. Moreover, a proper LS algorithm would use all data combined, that is, applying LS on all the links in one shot and not just summing them up (since the links are very similar (short links), the LS approach won't probably have much impact).

An important issue which arises is the phase unwrapping. Since the phase is measured through the complex signal, results in an a ambiguity. When the signal is under sampled (in frequency) or is noisy, it can cause the phase to not look like a linear line even though it really is. This sometimes causes "jumps" in the moisture level.

Stability of the Model

Figure 9A:
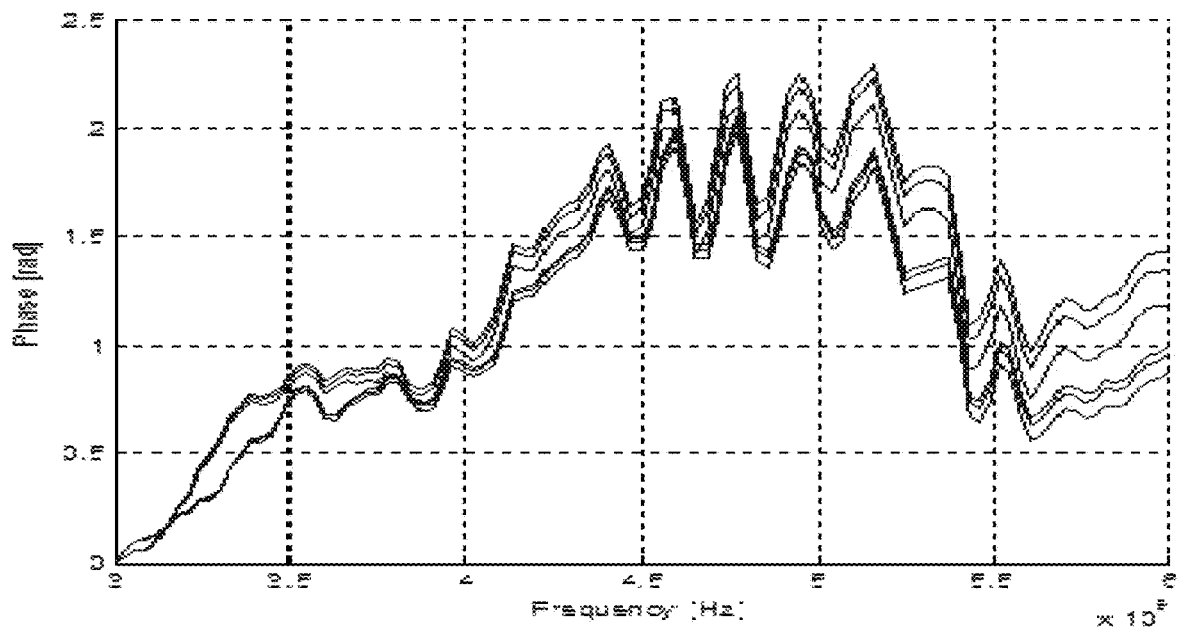
FIGS. 9A and 9B illustrate two examples of $\phi\_0$ (f) for a given link for different moisture differences, in accordance with examples.
Figure 9B:
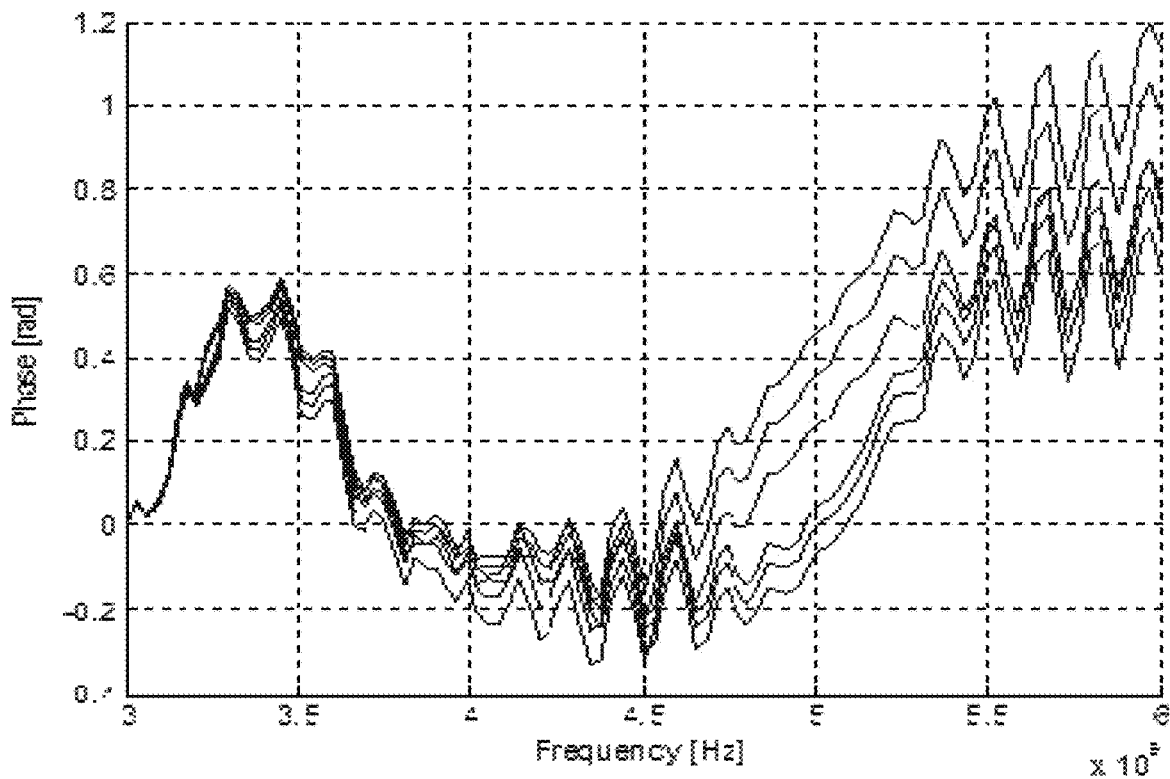

In some cases the estimation of the model parameters $\phi\_0$ (f) and a_2 are computed according to the following methods. FIGS. 9A and 9B illustrate two examples of $\phi\_0$ (f) for a given link for different moisture differences.

The $\phi\_0$ (f) is then averaged to provide the calibration for each link.

Figure 9C:
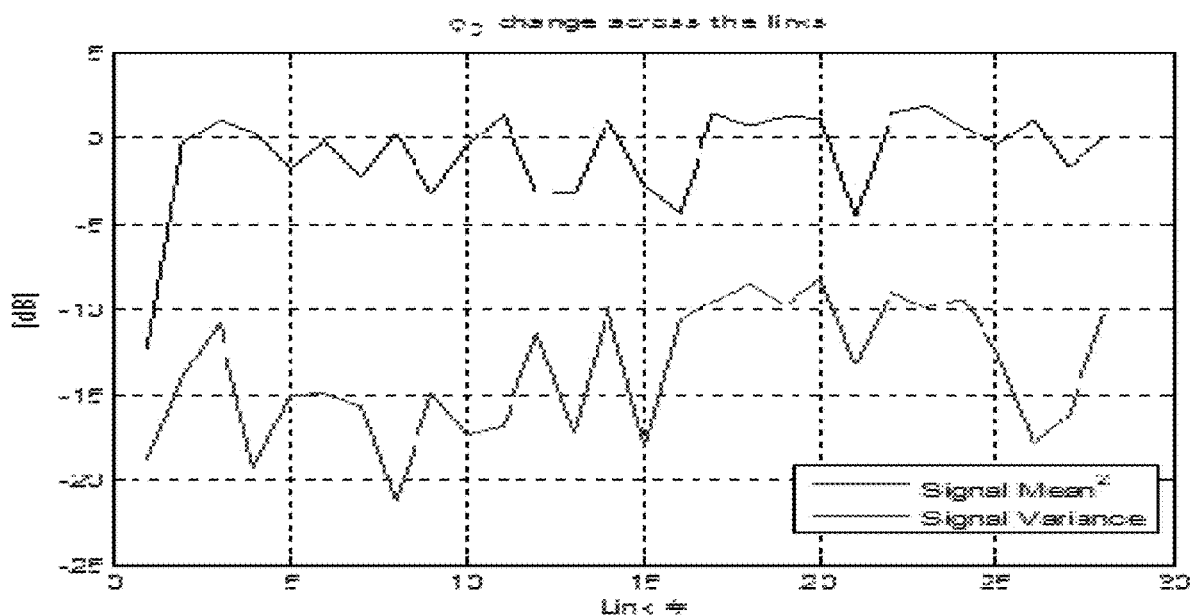
FIG. 9C is a graph illustrating the mean power of the function $\phi\_0$ (f) for each link and the variance of this function across the different combinations of moisture differences, in accordance with examples.
Figure 9D:
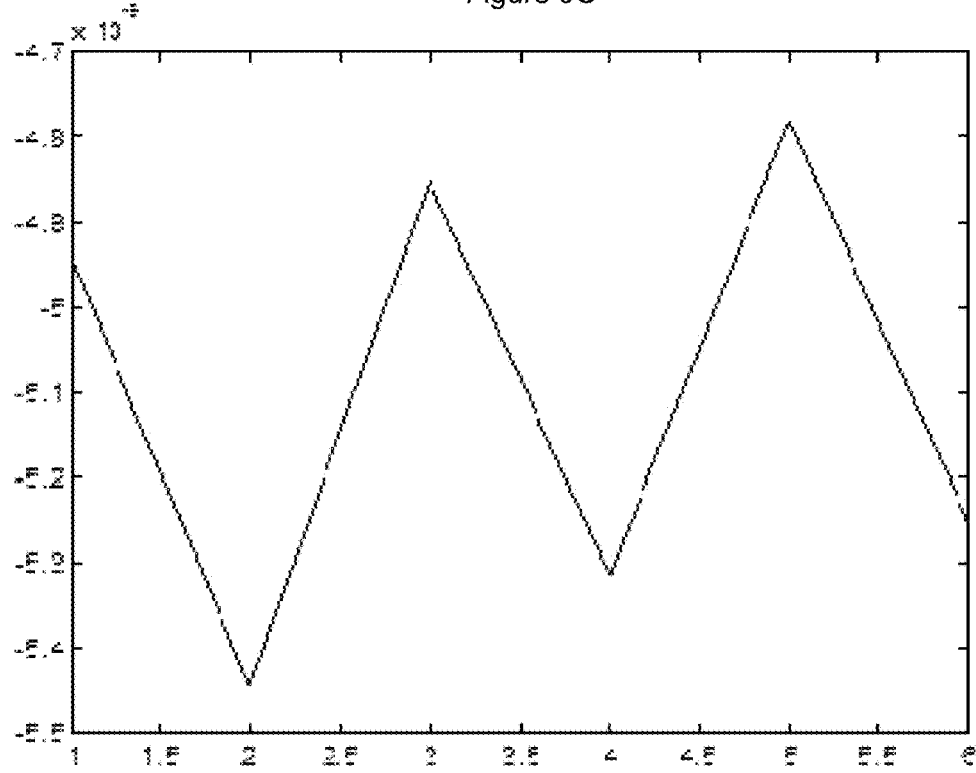
FIG. 9D is graph illustrating s the different values of the parameter $\alpha_2$ for links with the same distance after being averaged for different moisture differences, in accordance with examples.

FIG. 9C is a graph illustrating the mean power of the function $\phi\_0$ (f) for each link and the variance of this function across the different combinations of moisture differences.

It is clear from the graph of FIG. 9C that the variance of the function is lower than the mean power.

The values are around −5.1e-9 and pretty constant across the links with the same distance between tx and rx. A trivial model for this parameter would be that the phase slope is 2*pi*0.0275*sqrt(78)/3e8=5.0867e-09. The values are close so this is in good agreement with the theory!

In further embodiments, the processing unit may be a digital processing device including one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the system disclosed herein includes one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device.

In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media. In some embodiments, the system disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, the system disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the system disclosed herein includes one or more databases, or use of the same. In view of the disclosure provided herein, those of skill in the art will recognize that many databases are suitable for storage and retrieval of information as described herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are use, they should not be construed as necessarily limiting.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only. The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A system for measuring properties of soil, the system comprising:
    at least one probe configured and operable to be inserted into said soil;
    at least one Radio Frequency (RF) antenna array, said at least one RF antenna array comprising a plurality of antennas rigidly attached to said at least one probe for transmitting RF signals into the soil and receiving reflected RF signals;
    a radio link characterization unit configured and operable to:
        transmit the RF signals from an antenna selected out of said plurality of antennas; and
        receive the reflected RF signals at an at least one another antenna out of said plurality of antennas to yield at least one radio link, said radio link comprising propagation of the RF signals in said soil; and
    at least one processing unit configured and operable to convert characteristics of said at least one radio link into data relating to characteristics of properties of said soil.

2. The system of claim 1, wherein the plurality of antennas are divided into a plurality of transmitting antennas and a plurality of receiving antennas.

3. The system of claim 1, wherein one or more absorbing materials are placed between adjacent antennas of said plurality of antennas.

4. The system of claim 1, wherein the one or more absorbing materials are selected from the group consisting of: carbon; metallic particles embedded inside a foam or solid plastic.

5. The system of claim 1, comprising a protection seal made of electromagnetic transparent material for covering said device or said at least one Radio Frequency (RF) antenna array.

6. The system of claim 5, wherein said protection seal is made of plastic.

7. The system of claim 6, wherein said plastic is selected from the group consisting of: ABS, PVC, Polyethylene, Polypropylene, PTFE (Polytetrafluoroethylene).

8. The system of claim 1, wherein the at least one processing unit is configured with instructions to extract the amplitude and phase of said at least one radio link and compute a dielectric constant and conductivity of said soil to yield moisture or salinity of the soil in at least one layer of said soil.

9. The system of claim 1, wherein the plurality of antennas are selected from the group consisting of: monopole antennas, dipole antennas, microstrip patch antennas and slot antennas.

10. The system of claim 1, wherein the radio link characterization unit is selected from a group consisting of: a scalar network analyzer, vector network analyzer, an oscilloscope, a time domain reflectometer.

11. The system of claim 1, wherein said characteristics of properties of the soil comprise at least moisture content.

12. The system of claim 1, wherein said characteristics of properties of the soil comprise at least salinity content and moisture content.

13. The system of claim 1, wherein the shape of the at least one probe is selected from the group consisting of: rod, tube, pipe, pole, screw.

14. The system of claim 13, wherein the at least one probe is a screw, the screw comprising a screw thread having protrusions, and wherein the plurality of antennas are placed on the protrusions of the screw thread.

15. The system of claim 14, further comprising a communication module configured to transmit said at least one radio link characteristics or characteristics of the properties of the soil to an electronic device.

16. A method for measuring characteristics of properties of soil, the method comprising:
   transmitting one or more Radio Frequency (RF) signals into the soil from an antenna array, said antenna array comprising a plurality of antennas rigidly attached to at least one probe, said at least one probe is configured and operable to be inserted into said soil;
   receiving the reflected RF signals at least one another antenna out of said plurality of antennas to yield at least one radio link, said radio link comprising a propagation of the RF signals in said soil; and
   converting characteristics of said at least one radio link into the characteristics of the properties of the soil by at least one processing unit.

17. The method of claim 16, wherein said conversion comprising:
   extracting the amplitude and phase of said at least one radio link;
   calculating a dielectric constant and conductivity of the soil;
   calculating moisture or salinity of the soil in at least one layer of said soil.

18. The method of claim 17, comprising:
   measuring the soil at a plurality of layers within the soil over time; and
   generating a profile of the soil moisture or salinity according to the measured time and the soil layer being measured.

19. The method of claim 16 comprising dividing the plurality of antennas into a plurality of transmitting antennas and a plurality of receiving antennas.

20. The method of claim 16, comprising placing one or more absorbing materials between adjacent antennas of said plurality of antennas.

* * * * *